United States Patent
Hoda et al.

(10) Patent No.: US 12,116,285 B2
(45) Date of Patent: Oct. 15, 2024

(54) POROUS SILICA PARTICLE COMPOSITION

(71) Applicant: FUJI CHEMICAL INDUSTRIES CO., LTD., Nakaniikawa-gun (JP)

(72) Inventors: Koji Hoda, Nakaniikawa-gun (JP); Hiroshi Kawaguchi, Nakaniikawa-gun (JP); Teppei Shibata, Nakaniikawa-gun (JP); Tadashi Fukami, Nakaniikawa-gun (JP); Tadashi Yoshigai, Nakaniikawa-gun (JP); Tatsuki Ueno, Nakaniikawa-gun (JP); Yo Nakashima, Nakaniikawa-gun (JP); Tetsuya Oonuki, Nakaniikawa-gun (JP); Hitoshi Sakai, Nakaniikawa-gun (JP)

(73) Assignee: FUJI CHEMICAL INDUSTRIES CO., LTD., Nakaniikawa-gun (JP)

( * ) Notice: Subject to any disclaimer, the term of this patent is extended or adjusted under 35 U.S.C. 154(b) by 738 days.

(21) Appl. No.: 17/282,942

(22) PCT Filed: Oct. 4, 2019

(86) PCT No.: PCT/JP2019/039299
§ 371 (c)(1),
(2) Date: Apr. 5, 2021

(87) PCT Pub. No.: WO2020/071539
PCT Pub. Date: Apr. 9, 2020

(65) Prior Publication Data
US 2021/0380422 A1 Dec. 9, 2021

(30) Foreign Application Priority Data

Oct. 5, 2018 (JP) .................. 2018-189842
Mar. 25, 2019 (JP) .................. 2019-057003

(51) Int. Cl.
*C01B 33/193* (2006.01)
*A61K 9/10* (2006.01)
(Continued)

(52) U.S. Cl.
CPC .............. *C01B 33/193* (2013.01); *A61K 9/10* (2013.01); *A61K 9/513* (2013.01); *A61K 45/06* (2013.01);
(Continued)

(58) Field of Classification Search
CPC ........ C01B 33/193; A61K 9/10; A61K 9/513; A61K 45/06; C01P 2006/12;
(Continued)

(56) References Cited

U.S. PATENT DOCUMENTS

2009/0311321 A1 12/2009 Mimura et al.
2011/0104270 A1 5/2011 Yanagi et al.
(Continued)

FOREIGN PATENT DOCUMENTS

CN 101687632 A 3/2010
CN 103038168 A 4/2013
(Continued)

OTHER PUBLICATIONS

Sarawade, Pradip B., et al. "Synthesis of hydrophilic and hydrophobic xerogels with superior properties using sodium silicate." Microporous and mesoporous materials 139.1-3 (2011): 138-147.*
(Continued)

*Primary Examiner* — Richard M Rump
(74) *Attorney, Agent, or Firm* — Oblon, McClelland, Maier & Neustadt, L.L.P.

(57) ABSTRACT

A silica that is superior in terms of fluidity, oil absorption ability, and compression moldability to conventional silica used as a pharmaceutical additive, and is suitable as an additive for formulations such as pharmaceuticals. A porous
(Continued)

silica particle composition having the following properties: (1) a BET specific surface area from 250 to 1,000 m²/g; (2) an average particle diameter from 1 to 150 μm; (3) a pore volume from 0.1 to 8.0 cm³/g; and (4) an oil absorption capacity from 2.2 to 5.0 mL/g.

18 Claims, 6 Drawing Sheets

(51) Int. Cl.
  *A61K 9/51*     (2006.01)
  *A61K 45/06*    (2006.01)

(52) U.S. Cl.
  CPC ...... *C01P 2006/12* (2013.01); *C01P 2006/14* (2013.01); *C01P 2006/17* (2013.01); *C01P 2006/19* (2013.01)

(58) Field of Classification Search
  CPC .............. C01P 2006/14; C01P 2006/17; C01P 2006/19; B01J 20/103; B01J 20/28004; B01J 20/28011; B01J 20/28057; B01J 20/28069
  See application file for complete search history.

(56) References Cited

U.S. PATENT DOCUMENTS

| | | | |
|---|---|---|---|
| 2013/0196848 A1† | 8/2013 | Kretzschmar | |
| 2015/0366805 A1† | 12/2015 | Monsuur | |

FOREIGN PATENT DOCUMENTS

| | | | |
|---|---|---|---|
| CN | 108408732 A | 8/2018 | |
| CN | 108557828 A | 9/2018 | |
| EP | 0 361 622 B1 | 7/1995 | |
| JP | 52-126695 A | 10/1977 | |
| JP | 64-69509 A | 3/1989 | |
| JP | 6-40714 A | 2/1994 | |
| JP | 2006-306702 A | 11/2006 | |
| JP | 2011-206952 A | 10/2011 | |
| JP | 2014-88307 A | 5/2014 | |
| JP | 2015-13801 A | 1/2015 | |
| JP | 2015-91822 A | 5/2015 | |
| JP | 2015-113277 A | 6/2015 | |
| JP | 2016-508202 A | 3/2016 | |
| JP | 2017-14117 A | 1/2017 | |
| JP | 2017-512811 A | 5/2017 | |
| JP | 2018-24825 A | 2/2018 | |
| JP | 2018-27912 A | 2/2018 | |
| WO | WO 2008/018371 A1 | 2/2008 | |
| WO | WO 2010/001574 A1 | 1/2010 | |
| WO | WO 2015/150561 A2 | 10/2015 | |
| WO | WO 2016/129410 A1 | 8/2016 | |

OTHER PUBLICATIONS

Zong, Sekai, et al. "Characterization and comparison of uniform hydrophilic/hydrophobic transparent silica aerogel beads: skeleton strength and surface modification." Rsc Advances 5.68 (2015): 55579-55587.*
Office Action issued Sep. 28, 2021 in corresponding Indian Patent Application No. 202117015599 (with English Translation), 7 pages.
International Search Report issued Dec. 17, 2019 in PCT/JP2019/039299 filed Oct. 4, 2019, 2 pages.
Chaudhari, S., et al., "Mesoporous Silica as a Carrier for Amorphous Solid Dispersion", *British Journal of Pharmaceutical Research*, vol. 16, No. 6, 2017, pp. 1-19.
Choudhari, Y., et al., "Comparative evaluation of porous silica based carriers for lipids and liquid drug formulations", Mesoporous Biomater, vol. 1, 2014, pp. 61-74.
Japanese Office Action issued Jun. 21, 2022 that an anonymous third party filed a written submission of publications on May 30, 2022 for Japanese Patent Application No. 2020-551113 (with partial unedited computer generated English translation), 24 pages.
Japanese Office Action issued Jun. 28, 2022 in Japanese Patent Application No. 2020-551113 (with unedited computer generated English translation), 12 pages.
"Characteristics and Applications of Gel Method Silica", TOSOH Research & Technology Review Vo. 45 (2001), pp. 65-69 (with a partial unedited computer generated English translation).
"On the oil absorption of pigments", Colour Material vol. 37, No. 7 (1964), pp. 259-263(with a partial unedited computer generated English translation).
Web output screen showing the issue date of Publication 2, Colour Material vol. 37, No. 7 (1964), 2 pages in total (with a partial unedited computer generated English translation).
Product catalogue "High-performance Micro-sphere Fine Silica Sunsphere", Asahi Glass SI-Tech. Co., Ltd. (2005), 12 pages in total.
Characteristics of High Performance Microspherical Silica, "Sunsphere®", and its Application for Cosmetics, Res. Reports Asahi Glass Co., Ltd., 61 (2011) pp. 37-41 (with a partial unedited computer generated English translation).
Japanese Office Action issued Jul. 26, 2022 that an anonymous third party filed a written submission of publications on Jun. 30, 2022 for Japanese Patent Application No. 2020-551113 (with a partial machine translation), 11 pages.
Extended European Search Report issued May 16, 2022 in European Patent Application No. 19869681.7, 7 pages.
Combined Chinese Office Action and Search Report issued on Mar. 13, 2023 in Chinese Patent Application No. 201980065441.0 (with English translation), 27 pages.

\* cited by examiner
† cited by third party

POROUS SILICA PARTICLE COMPOSITION

TECHNICAL FIELD

The present invention relates to a novel porous silica particle composition, more specifically, particle powder of porous silicon dioxide, applications thereof, and a pharmaceutical formulation, a cosmetic product, a health food, or a supplement containing the composition.

BACKGROUND ART

Silica, that is, silicon dioxide ($SiO_2$) may also be referred to as silicic anhydride, silicic acid, or silicon oxide. Pure silica is colorless and transparent and is also present widely distributed in nature.

Synthetic products thereof are used in various fields of the industry. For example, they are used as a drying agent to preserve foods or precision equipment of semiconductors, and are also used as a deodorant, an agriculture fertilizer, and a moisture conditioning agent for buildings. Alternatively, they are also used as an abrasive for electronic material substrate, silicon wafer, and the like, and are utilized in various fields such as raw materials for products such as bakeware, experimental instruments, light fiber, enamel, silica cement, ceramics, and tires; a liquid chromatography carrier; or surface treatment agents for the surface of light bulbs or CRT displays; and penetration inhibitors for printing ink of newspapers.

Among them, in the pharmaceutical field, silica may also be referred to as hydrated silicon dioxide, light silicic anhydride, silicon dioxide, colloidal silicon dioxide, hydrated colloidal silica, or anhydrous colloidal silica, and used in a lot of applications such as an adsorbent, a fluidizer, an agglomeration preventing agent, a lubricant, a disintegrant, a heat stabilizer, a suspending agent, an emulsion stabilizer, and a thickening agent.

In particular, porous silica particle compositions having pores have recently attracted attention as a pharmaceutical carrier for solid drugs and oily drugs which are poorly soluble in water, and some cases where these compositions have effects on the solubility of drugs or the dissolution of drugs are also reported (Patent Literatures 1 and 2 and Non Patent Literatures 1 and 2).

Examples of known methods for masking the bitterness of a drug include a method of modulating the taste on the tongue by a sweetening agent or a taste masking agent, and a method of coating drug-containing particles with a polymer, a sugar, and the like. Examples of the coating method include a method of granulating a mixture of a mitiglinide calcium hydrate which is an active ingredient having bitterness with crystalline cellulose while spraying a solution of a masking agent such as aminoalkyl methacrylate copolymer E, polyvinylacetal diethylaminoacetate, ethyl acrylate-methyl methacrylate copolymer, or ethyl cellulose by a high-speed stirring granulation method (Patent Literature 3), and bitter drug-coated particles in which a layer containing a drug is formed on the outer layer of a nucleating agent made of crystalline cellulose and a coating layer such as a polymer is further formed on the outer layer (Patent Literature 4).

CITATION LIST

Patent Literature

Patent Literature 1: JP 2017-14117
Patent Literature 2: JP 2017-512811
Patent Literature 3: WO 2008/018371
Patent Literature 4: WO 2010/001574

Non-Patent Literature

Non-Patent Literature 1: British Journal of Pharmaceutical Research. 2017:16(6), 1-19
Non-Patent Literature 2: Mesoporous Biomater. 2014:1, 61-74

SUMMARY OF INVENTION

Problem

However, these silica particle compositions having pores are not considered to improve compression moldability in making a tablet by using silica from the viewpoint of applicability to all formulations, and thus it must be said that these compositions are still insufficient in terms of applicability to all formulations.

In general, when a silica particle composition is used in the tablet as an adsorption carrier of a drug or the like, it has a high drug stability due to its neutrality, but has excessively high specific volume to decrease compression moldability, resulting in a problem of a limitation of the amount to be contained.

In fact, while a large number of porous silica particle compositions are commercially available as pharmaceutical additives, they are not satisfactory in terms of flowability and oil absorption capacity, and the compression moldability when added to the tablet or the like, and thus further excellent silica is strongly desired.

The problems of the silica particle composition as such pharmaceutical additives also apply to additives for cosmetic, health food, or supplement, and the silica having further excellent moldability and the like has been desired.

Further, from the viewpoint of the bitterness masking of a bitter drug, there are problems as follows: roughness feeling is caused in the mouth in a method of using a nucleating agent due to a large size of medication-containing particles; the formation of particles having a sufficient strength is difficult in a method of forming drug-containing particles; a large manufacturing time is required for forming each layer such as a coating layer and for carrying and impregnating a drug; heating and removal of water are required upon granulation since when the amount of a drug or the amount of coating ingredients are increased, a higher amount of water is required for dissolving and dispersing such ingredients; and the like.

Solution to Problem

The present inventors have energetically conducted studies to solve the problems of the silica particle composition in the fields of pharmaceutical and food additives as indicated above, and as a result, have found that a porous silica particle composition which is excellent in oil absorption capacity, compression moldability, and flowability, improves various problems such as disintegration, and further excellent in masking of a bitter drug or dissolution of a drug, thereby completing the present invention.

The present invention provides the following [1] to [34].

[1] A porous silica particle composition having the following properties:
(1) a BET specific surface area from 250 to 1,000 $m^2/g$;
(2) an average particle diameter from 1 to 150 µm;

(3) a pore volume from 0.1 to 8.0 cm³/g; and
(4) an oil absorption capacity from 2.2 to 5.0 mL/g.

[2] The porous silica particle composition according to [1], wherein
(1) the BET specific surface area is from 250 to 1,000 m²/g;
(2) the average particle diameter is from 10 to 150 μm;
(3) the pore volume is from 0.1 to 8.0 cm³/g; and
(4) the oil absorption capacity is from 2.2 to 5.0 mL/g.

[3] The porous silica particle composition according to [1], wherein
(1) the BET specific surface area is from 250 to 700 m²/g;
(2) the average particle diameter is from 1 to 40 μm;
(3) a static specific volume is from 8 to 40 mL/g;
(4) the oil absorption capacity is from 2.2 to 5.0 mL/g; and
(5) a water absorption capacity is from 2.2 to 5.0 mL/g.

[4] The porous silica particle composition according to [1] or [3], wherein the average particle diameter is from 1 to 30 μm and a shape is substantially non-spherical.

[5] The porous silica particle composition according to any one of [1], [3], and [4], wherein the average particle diameter is from 1 to 10 μm and the shape is substantially non-spherical.

[6] The porous silica particle composition according to [1] or [2], wherein
(1) the BET specific surface area is from 250 to 700 m²/g;
(2) the average particle diameter is from 20 to 150 μm;
(3) a static specific volume is from 4 to 10 mL/g;
(4) the oil absorption capacity is from 2.2 to 5.0 mL/g; and
(5) a water absorption capacity is from 2.2 to 5.0 mL/g.

[7] The porous silica particle composition according to any one of [1] to [5], wherein a static specific volume is from 20 to 40 mL/g.

[8] The porous silica particle composition according to any one of [1] to [7], wherein the composition is amorphous.

[9] The porous silica particle composition according to any one of [1] to [8], wherein the composition is a powder.

[10] The porous silica particle composition according to any one of [1] to [9], wherein the pore volume is from 1.0 to 2.5 cm³/g.

[11] The porous silica particle composition according to any one of [1] to [10], wherein a pore mode diameter is from 20 to 150 nm.

[12] The porous silica particle composition according to any one of [1] to [11], wherein a relative width of a pore size distribution is from 20 to 120 nm.

[13] The porous silica particle composition according to any one of [1] to [12], comprising a plate-like silica particle having a particle diameter from 20 to 500 nm and a spherical silica particle having a particle diameter from 5 to 50 nm.

[14] The porous silica particle composition according to any one of [1] to [13], which is tabletable without tableting problems when the porous silica particle composition alone is tableted.

[15] The porous silica particle composition according to any one of [1] to [14], wherein the oil absorption capacity is from 2.4 to 4.5 mL/g.

[16] The porous silica particle composition according to any one of [1] to [6] and [8] to [15], wherein the static specific volume is from 4.5 to 8 mL/g.

[17] The porous silica particle composition according to any one of [1] to [16], wherein the BET specific surface area is from 280 to 650 m²/g.

[18] The porous silica particle composition according to any one of [1] to [17], wherein the pore volume is from 1.5 to 2.5 cm³/g.

[19] The porous silica particle composition according to any one of [1] to [18], wherein the pore mode diameter is from 35 to 130 nm.

[20] The porous silica particle composition according to any one of [1] to [19], wherein the relative width of the pore size distribution is from 20 to 70 nm.

[21] The porous silica particle composition according to any one of [1], [2], and [6] to [20], wherein the average particle diameter is from 30 to 120 μm.

[22] The porous silica particle composition according to any one of [1] to [3] and [6] to [21], wherein a lower limit of the average particle diameter is 30 μm.

[23] The porous silica particle composition according to any one of [1], [2], and [6] to [22], wherein the lower limit of the average particle diameter is 45 μm.

[24] The porous silica particle composition according to any one of [1] to [23], wherein sphericity of the particle is from 0.8 to 1.0.

[25] The porous silica particle composition according to any one of [1] to [24], wherein the composition is a pharmaceutical excipient.

[26] The porous silica particle composition according to any one of [1] to [25], wherein the composition adsorbs an active pharmaceutical ingredient.

[27] The porous silica particle composition according to any one of [1] to [24], wherein the composition is an excipient for a supplement, a health food, or a cosmetic.

[28] An additive for a pharmaceutical, a supplement, a health food, or a cosmetic in which the additive comprises the porous silica particle composition according to any one of [1] to [24].

[29] A pharmaceutical formulation, supplement, health food, or cosmetic product comprising the porous silica particle composition according to any one of [1] to [24].

[30] A pharmaceutical composition comprising the porous silica particle composition according to any one of [1] to [24], a polymer, and a bitter drug.

[31] The pharmaceutical composition comprising a bitter drug according to [29], wherein the pharmaceutical composition is obtained by coating the porous silica particle according to any one of [1] to [24] with a polymer.

[32] A pharmaceutical composition comprising the porous silica particle according to any one of [1] to [24], wherein the pharmaceutical composition comprises a polymer in which a bitter drug is dispersed.

[33] A solid dispersion obtained by dispersing an active pharmaceutical ingredient in the porous silica particle composition according to any one of [1] to [24].

[34] A solid dispersion wherein (1) the porous silica particle composition according to [4] or [5] having a substantially non-spherical shape, or (2) the porous silica particle composition according to any one of [1] to [3] and [6] to [24] having the average particle diameter from 10 to 150 μm and a substantially spherical shape, and an active pharmaceutical ingredient disperses.

Advantageous Effects of Invention

The present invention provides a porous silica particle composition which is excellent in oil absorption capacity, compression moldability, flowability, and the like, and may further improve the disintegration of a tablet after compression molding; and the porous silica particle powder; as well as an excipient consisting of the porous silica particle composition; and a pharmaceutical formulation, a supplement, a health food, a cosmetic product, and a solid dispersion comprising the porous silica particle composition; and the porous silica particle composition which adsorbs an active pharmaceutical ingredient; and further, a pharmaceutical formulation containing the porous silica particle composition which masks the bitterness of a bitter drug.

DESCRIPTION OF EMBODIMENTS

Figure 1:
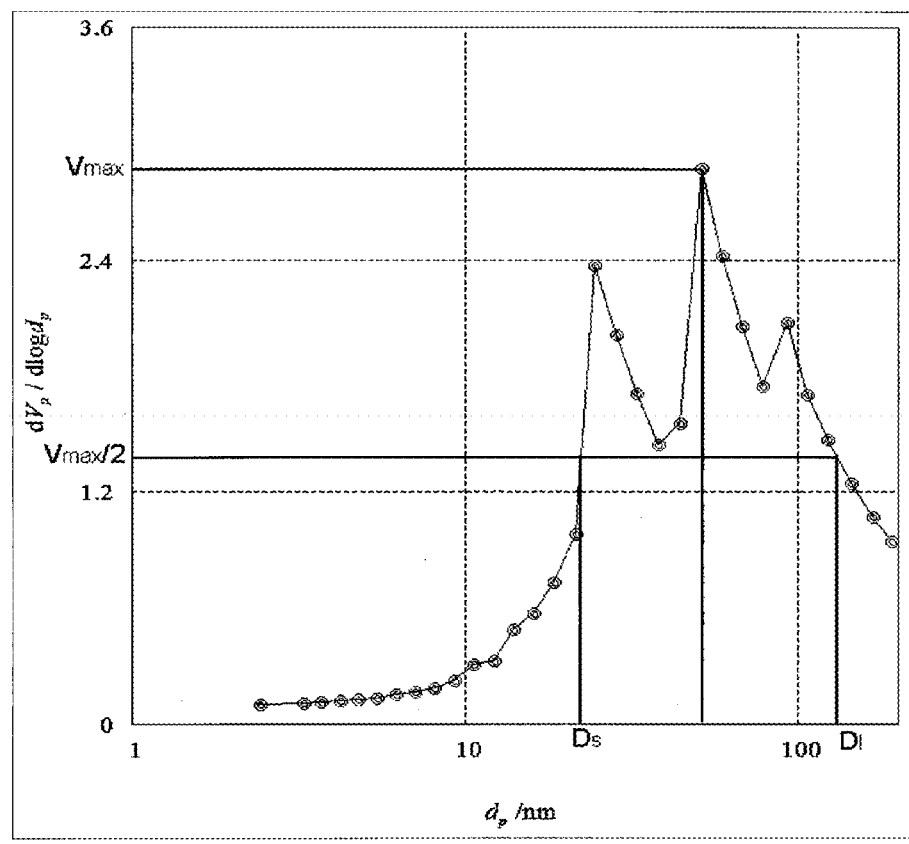
FIG. 1 is a graph showing a calculation method of the relative width of the pore size distribution.

The porous silica particle composition of the present invention refers to, when silica particles formed in a production liquid by the production method described below are defined as primary particles, those formed after drying of the production liquid, including a particle composition constituted of agglomeration, bonding, and the like of plate-like silica primary particles and/or granular silica primary particles, and further including a particle composition obtained by pulverizing the particle composition within its scope. It has broad macropores (porosity) throughout the composition and also has a high BET specific surface area, a high pore volume, a high oil absorption capacity, and an excellent compression moldability.

The porous silica particle composition of the present invention means the above silica particles or the composition thereof or an aggregate of various silica particle compositions and has the following properties of (1) to (4) as the aggregate and additionally has the features mentioned below. The present aggregate substantially has a powder shape and may generically be referred to as silica particles. The particle shape of the porous silica particle composition of the present invention is spherical, or non-spherical such as agglomerated shape, plate-like, or undefined shape. The porous silica particle composition of the present invention is amorphous silica. Since the porous silica particle composition shows no peak characteristic to crystalline silica and shows a halo pattern by XRD, it can be confirmed to be amorphous.

Specifically, the porous silica particle composition of the present invention has the following powder properties:
 (1) a BET specific surface area from 250 to 1,000 $m^2/g$;
 (2) an average particle diameter from 10 to 150 μm;
 (3) a pore volume from 0.1 to 8.0 $cm^3/g$; and
 (4) an oil absorption capacity from 2.2 to 5.0 mL/g.

The BET specific surface area is an index for specifying the porous nature of the silica and is commonly used in general. The BET specific surface area of the porous silica particle composition of the present invention is usually in a range from 250 to 1,000 $m^2/g$, preferably in a range from 250 to 700 $m^2/g$, more preferably in a range from 280 to 650 $m^2/g$, and further preferably in a range from 280 to 500 $m^2/g$.

The average particle diameter of the porous silica particle composition of the present invention is a median diameter (D50) and is specifically, in a range from 1 to 150 μm, preferably in a range from 10 to 150 μm, more preferably in a range from 20 to 150 μm, further preferably in a range from 30 to 150 μm, and even more preferably in a range from 30 to 120 μm. Among them, from the viewpoint of bitterness masking, the average particle diameter of the porous silica particles to be used is preferably from 45 to 150 μm, and more preferably in a range from 45 to 120 μm. The average particle diameter in a non-spherical or substantially non-spherical porous silica particle composition of the present invention is preferably in a range from 1 to 10 μm, and more preferably in a range from 1.5 to 8 μm.

The pore volume is also one of the indexes for specifying the porous nature of the silica and is commonly used in general. The pore volume of the porous silica particle composition of the present invention is preferably in a range from 0.1 to 8.0 $cm^3/g$, more preferably in a range from 1.0 to 3.0 $cm^3/g$, further preferably in a range from 1.0 to 2.5 $cm^3/g$, and particularly preferably in a range from 1.5 to 2.5 $cm^3/g$. The pore volume can be determined by the BJH method.

The oil absorption capacity is also one of the indexes for specifying the porous nature of the silica and is commonly used in general. The oil absorption capacity of the porous silica particle composition of the present invention is preferably in a range from 2.2 to 5.0 mL/g, more preferably in a range from 2.4 to 4.5 mL/g, and further preferably in a range from 3.0 to 4.5 mL/g. The porous silica particle composition of the present invention hardly causes a decrease in flowability even when a high content of oil is absorbed, and has properties of hardly causing exudation of oil even when being compression molded.

In addition to the above, examples of the properties for specifying the porous silica particle composition of the present invention include water absorption capacity, static specific volume, and dynamic specific volume.

The water absorption capacity of the porous silica particle composition of the present invention is preferably in a range from 2.2 to 5.0 mL/g, more preferably in a range from 2.4 to 4.5 mL/g, and further preferably in a range from 3.0 to 4.5 mL/g.

Preferred examples of the static specific volume of the porous silica particle composition of the present invention include those in a range from 4 to 40 mL/g, more preferably those in a range from 4 to 10 mL/g, further preferably those in a range from 4.5 to 8 mL/g, and particularly preferably those in a range from 4.5 to 7 mL/g. The static specific volume in the non-spherical porous silica particle composition of the present invention is preferably in a range from 9 to 40 mL/g, and more preferably in a range from 10 to 35 mL/g.

Preferred examples of the dynamic specific volume of the porous silica particle composition of the present invention include those in a range from 3 to 30 mL/g, more preferably those in a range from 3 to 9 mL/g, further preferably those in a range from 3.5 to 6.5 mL/g, and particularly preferably those in a range from 4 to 6 mL/g. The dynamic specific volume in the non-spherical porous silica particle composition of the present invention is preferably in a range from 6 to 30 mL/g, and more preferably in a range from 7 to 25 mL/g.

In addition to the above properties, the pH of the porous silica particle composition of the present invention is usually in the neutral region and can be measured as the pH when suspended in water. Specifically, when it is formed into a 5% (W/V) suspension, the pH is usually in a range from 6 to 8.

The porous silica particle composition of the present invention includes primary particles having different shapes such as plate-like and spherical, and is preferably formed through the further agglomeration of secondary particles in which the primary particles are agglomerated and bonded together. Such an agglomeration and bonding structure of the secondary particles can be confirmed from the measurement results of the pore size distribution obtained by FE-SEM or SEM photographic observation, or the nitrogen adsorption method. The shape of the primary particles can be observed from an SEM photograph at a magnification of 10,000 times or more, and can be basically classified into plate-like and spherical. Here, plate-like refers to a partially planar shape such as plate-shaped, strip-shaped, and scaly. In addition, spherical refers to one having a shape of grain as a whole. Such primary particles can be observed in the randomly agglomerated, bonded, and overlapped state. As can be seen from the FE-SEM or SEM photographic observation, the size of the above plate-like particles is in a range from 20 to 500 nm in mean diameter at the plate surface direction and in a range from 10 to 50 nm in thickness. Further, the size of the above spherical particles is in a range from 5 to 50 nm in particle diameter.

Pulverizing and finely grinding of the agglomerated and bonded secondary particles described above allows to obtain the substantially non-spherical porous silica particle composition as described above.

In the present invention, such agglomerated and bonded secondary particles and pulverized particles can be separately or appropriately mixed and used in accordance with the intended use.

The pore size distribution of the porous silica particle composition of the present invention preferably has two or three pore peaks in a range from 1 to 200 nm in pore diameter and is a broad peak shape in which the pore diameter of the lowest end and the highest end of multiple peaks ranges from 20 to 200 nm. When the porous silica particle composition has two pore peaks, the top of each peak is preferably in a range from 10 to 40 nm and from 35 to 70 nm, and the top of each peak is more preferably in a range from 15 to 35 nm and in a range from 40 to 60 nm. When the porous silica particle composition has three pore peaks, the top of each peak is preferably in a range from 10 to 40 nm, 35 to 70 nm, and 70 to 150 nm, and more preferably in a range from 15 to 35 nm, 40 to 60 nm, and 80 to 130 nm. Among these two or more pore peaks, the pore diameter of the highest top is the mode diameter of the pore size distribution and it is preferably in a range from 20 to 150 nm, more preferably in a range from 35 to 130 nm, and further preferably in a range from 35 to 65 nm. Examples of the detailed measurement method and measurement conditions of the pore size distribution include those described in Examples mentioned below.

Since having multiple pore peaks for the pore diameter, the porous silica particle composition of the present invention has a broad pore size distribution and the relative width of the pore size distribution defined as mentioned below is preferably in a range from 20 to 120 nm, and more preferably in a range from 20 to 70 nm. The relative width of the pore size distribution may be obtained by determining a value ½ of the height of the mode diameter peak of the pore size distribution, determining the largest pore diameter (Dl) and the shortest pore diameter (Ds) which take the above value, and then determining the difference between them (Dl-Ds). Next, the difference may be divided by the height of the mode diameter peak of the pore size distribution to determine the value. The detailed calculation formula is shown in Examples mentioned below. In the present invention, the shape of the pore size distribution may be determined by setting the pore diameter as the horizontal axis and the volume distribution as the vertical axis in the pore size distribution chart measured by the BJH method.

The reason why the porous silica particle composition of the present invention has two or three pore peaks is considered to be that the composition has plate-like primary particles and spherical primary particles as basic building blocks and has multiple pores such as pores between plate-like primary particles, pores between spherical primary particles, and pores between plate-like primary particles and spherical primary particles.

The porous silica particle composition of the present invention can include those having spherical and non-spherical shapes by subjecting to granulation such as spray drying, drying method, pulverizing step, and the like.

Specifically, a substantially spherical silica particle composition can be produced by further drying granules obtained by spray drying.

The sphericity of the spherical granules is preferably in a range from 0.8 to 1.0, more preferably in a range from 0.85 to 1.0, and further preferably in a range from 0.9 to 1.0. The sphericity can be calculated by determining short diameter/long diameter from the SEM photograph.

Meanwhile, a method of producing a non-spherical silica particle composition may be in accordance with the above method.

The average particle diameter of the porous silica particle composition of the present invention is preferably in a range from 1 to 150 μm, and the particle diameter can be appropriately selected in accordance with granulation, powderization, and pulverization. The average particle diameter of the spherical granules of the porous silica particle composition of the present invention is preferably from 10 to 150 μm, more preferably from 20 to 150 μm, and even more preferably in a range from 30 to 120 μm. Among them, when the porous silica particle composition of the present invention is a substantially non-spherical silica particle composition, the average particle diameter is preferably from 1 to 40 μm, more preferably 1 to 10 μm, and further preferably from 1 to 8 μm.

In the present invention, the average particle diameter is a median diameter (D50) by volume and can be measured by using a dry or wet laser diffraction/scattering type particle size measuring apparatus. Examples of the detailed measurement conditions include those described in Examples mentioned below.

The granules of the porous silica particle composition of the present invention have a high flowability, and when the measurement is carried out based on the measurement method of the flow rate through an orifice described in USP <1174>POWDER FLOW section, the orifice diameter, which is an index of the flowability, is preferably within a range from 4 to 12 mm, and more preferably within a range from 4 to 9 mm.

The value of the water content of the porous silica particle composition of the present invention may be vary in accordance with the measurement method. Specifically, it is based on either loss on drying or loss on ignition. The water content by loss on drying of the porous silica particle composition of the present invention is preferably within a range from 0.1 to 21%, more preferably within a range from 0.1 to 15%, and further preferably within a range from 0.1 to 7%. The water content by loss on ignition of the porous silica particle composition of the present invention is preferably within a range from 0.1 to 8.5%, and more preferably within a range from 0.1 to 7%. Measurement methods of both loss on drying and loss on ignition are described in the United States Pharmacopeia, and the water content can be determined in accordance with the methods.

The silicon dioxide ($SiO_2$) content of the porous silica particle composition of the present invention is preferably in a range from 95 to 100%, and more preferably in a range from 99 to 100%. The silicon dioxide content can be determined by the quantification method of silicon dioxide of the United States Pharmacopeia-National Formulary (USP-NF).

Next, a method of producing the porous silica particle composition of the present invention will be described.

The production method consists of the following step (1) to step (5).
(1) a step (1) of mixing and reacting a calcium source and a silicic acid source (a) in an aqueous solvent;
(2) a step (2) of mixing and reacting a reaction solution obtained in step (1) and a silicic acid source (b);
(3) a step (3) of mixing and reacting a reaction solution obtained in step (2) and a mineral acid;
(4) a step (4) of filtering and washing a reaction solution obtained in step (3); and
(5) a step of drying the washed product obtained in the step (4).

The step (1) may be carried out by any of adding an aqueous solution of the calcium source to an aqueous solution of the silicic acid source (a), adding an aqueous solution of the silicic acid source (a) to an aqueous solution of the calcium source, or simultaneously adding an aqueous solution of the silicic acid source (a) and an aqueous solution of the calcium source. The method of adding the aqueous solution of the silicic acid source (a) to the aqueous solution of the calcium source is preferable.

Examples of the calcium source include inorganic calcium salts such as calcium chloride and calcium nitrate, and calcium hydroxides. Examples of inorganic acids include hydrochloric acid, nitric acid, sulfuric acid, and carbonic acid. A solution obtained by mixing sodium hydroxide with these inorganic calcium salts can be used. Alternatively, a solution obtained by reacting a calcium hydroxide such as hydrated lime and the aforementioned inorganic acid in an arbitrary ratio can be used. The calcium concentration of an aqueous calcium salt solution is in a range from 0.1 to 10% in terms of calcium.

Examples of the silicic acid source (a) include aqueous solutions of sodium silicate, potassium silicate, and lithium silicate. As sodium silicate, No. 1 sodium silicate, No. 2 sodium silicate, No. 3 sodium silicate, or a natural silicate mineral dissolved in caustic soda can be used, and No. 3 sodium silicate is preferably used from the industrial viewpoint. The concentration of the silicic acid source (a) is in a range from 1 to 32% in terms of silicon dioxide.

The amounts of the above calcium source and silicic acid source used are defined by the blend ratio of the silicic acid source to the calcium source, and is in a range of calcium:silicon dioxide=from 1:0.5 to 1:2 in terms of molar ratio of calcium and silicon dioxide. The reaction temperature in this step is usually in a range from 15 to 80° C.

The step (2) can be carried out by adding an aqueous solution of the silicic acid source (b) to the reaction solution obtained in the step (1), adding the reaction solution obtained in the step (1) to an aqueous solution of the silicic acid source (b), or simultaneously adding the reaction solution obtained in the step (1) and an aqueous solution of the silicic acid source (b).

As the silicic acid source (b), those described as the above silicic acid source (a) can be used. Those having a silicate salt concentration in the same range as the above silicic acid source (a) can be used. The amount of the silicic acid source (b) to be added is defined by the blend ratio of the silicic acid source (b) to the calcium source of the step (1), and is in a range of calcium:silicon dioxide=from 1:2 to 1:6, and preferably from 1:3 to 1:5 in terms of molar ratio of calcium and silicon dioxide. The reaction temperature in this step is usually in a range from 30° C. to 100° C.

In the step (3), the reaction solution obtained in the step (2) may be reacted with the mineral acid.

Examples of the mineral acid include hydrochloric acid, sulfuric acid, nitric acid, and phosphoric acid, and preferred examples thereof include nitric acid. The concentration of the mineral acid to be used is 5 to 50%. The reaction can usually be carried out by adding the mineral acid to the reaction solution obtained in the step (2). The rate of adding the mineral acid may be appropriately set in accordance with the production facility or the production amount. The reaction temperature in this step is usually from 30° C. to 100° C.

In the step (4), the reaction solution obtained in the step (3) may be filtered and washed with water. As the washing methods for removing impurities such as calcium, methods such as decantation, filter press, and filtration which are usually industrially carried out, can be used. The end point of washing may be determined by the pH or the conductivity of the wash solution. Washing can be carried out in a range from 0 to 40° C.

In the step (5), the product filtered and washed in the step (4) may be dried to remove water.

Examples of drying methods include spray drying, fluidized granulation, fluidized bed granulation and drying, stirring granulation and drying, flash jet drying, drum drying, wet extrusion granulation and drying, shelf drying, reduced-pressure drying, and freeze drying. Since drying and a granulation step can be simultaneously and continuously carried out, spray drying is preferable. A drying method by heating is carried out at a drying temperature in a range from 80 to 500° C.

The conditions of spray drying are not particularly limited and a disc, Kestner, or nozzle spray dryer may be used as a spray dryer. Regarding the temperature of spray drying, it is preferably carried out at an inlet temperature in a range from about 150 to 400° C. and at an outlet temperature in a range from about 90 to 200° C.

As another drying method, drying can be carried out by reduced-pressure drying or the like after water is removed by adding an organic solvent or solvent replacement. It is also possible to make the oil absorption capacity, the specific surface area, and the specific volume higher than that of porous silica compositions obtained by the above heat drying methods.

After the drying step described above, pulverization is carried out if necessary, followed by sieving, classifying, and the like, thereby obtaining the porous silica particle composition of the present invention having the desired particle diameter. As the pulverization method, dry pulverization is preferable, where a jet mill, a ball mill, a roll mill, a hammer mill, a pin mill, or the like can be used. When particles having a particle diameter from 1 to 10 μm are obtained, a jet mill is preferably used.

The fine grinding and pulverization of the product obtained after filtering and washing in the step (4) can result in the efficiency of operations in modulating physical properties such as specific volume and flowability and carrying out drying and granulation in the step (5). The pulverization method is preferably wet pulverization, and it can be carried out by using, for example, a pulverizer such as a high-pressure homogenizer such as Star Burst (product name, manufactured by SUGINO MACHINE LIMITED), Nanomizer (product name, manufactured by SG Engineering. CO., LTD.), Ultimaizer (product name, manufactured by SUGINO MACHINE LIMITED, Karasawa Fine Co., Ltd.), Microfluidizer (product name, manufactured by MIZUHO INDUSTRIAL CO., LTD.), and Gaulin Homogenizer, a bead mill, a disc mill, and a homomixer.

The porous silica particle composition of the present invention can be used for the same applications as those in which conventional silica has been used so far. For example, it can be used as an additive for pharmaceutical, specifically, as an excipient, an adsorbent, a fluidizer, an agglomeration preventing agent, a lubricant, a disintegrant, a heat stabilizer, an emulsion stabilizer, a suspending agent, or a thickening agent. When used as the excipient, the fluidizer, the agglomeration preventing agent, the lubricant, the disintegrant, or the heat stabilizer, the porous silica particle composition of the present invention can be mixed with pharmaceutical additives such as other excipients, disintegrants, binders, and lubricants, and active pharmaceutical ingredient ingredients if necessary, and compression molded into a tablet. It can also be mixed and granulated into powders or granulated pharmaceuticals in the same manner. Further, the porous silica particle composition of the present invention can be granulated with the active pharmaceutical ingredient to give a spherical material for tableting, which is mixed into a base such as a solution, a suspension, an ointment, and a formulation such as cream, and kneaded to obtain the desired solution, suspension, ointment, or cream formulation. Alternatively, the porous silica particle composition of the present invention and the active pharmaceutical ingredient and, if necessary, other additives can be mixed into the above base and kneaded to obtain the desired solution, suspension, ointment, or cream formulation.

Regarding the blend ratio of each of them, based on 100 parts by weight of the porous silica particle composition, from 0.01 to 10,000 parts by weight of one or more ingredients of other pharmaceutical additives selected from the group consisting of an excipient, a disintegration aid, a bonding aid, a surfactant, a lubricant, an acidulant, a sweetener, a taste masking agent, a fragrance, a colorant, a stabilizing agent, and a foaming agent, and from 0.1 to 1,000 parts by weight of the active pharmaceutical ingredient may be blended.

In the present invention, the active pharmaceutical ingredient may be used in combination with the porous silica particle composition of the present invention in accordance with the administration route, and specific examples thereof include agents for the central nervous system such as a peripheral nerve agent, an antipyretic analgesic antiinflammatory agent, a sedative hypnotic agent, and a psychoneurotic agent; skeletal muscle relaxants, agents for the peripheral nerve system; agents for circulatory organs such as an antiarrhythmic agent, a diuretic, and a vasodilator; agents for respiratory organs such as a bronchodilator and an antitussive agent; agents for the gastrointestinal tract such as a digestive, an antiflatulent, and an antacid; metabolic agents such as a hormonal agent, an antihistamine agent, and a vitamin agent; antiulcer agents; antibiotics; and crude drug extracts. Hereinafter, representative names of the active pharmaceutical ingredient will be exemplified.

Examples of the antipyretic analgesic antiinflammatory agent include aniline derivatives such as pranlukast hydrate, and salicylic acid derivatives such as aspirin.

Examples of the bronchodilator include ephedrine hydrochloride.

Examples of the antitussive agent include codeines such as codeine phosphate.

Examples of an expectorant include potassium guaiacolsulfonate.

Examples of an antitussive expectorant include guaifenesin.

Examples of a psychotropic drug include chlorpromazine and reserpine.

Examples of an antidepressant include maprotiline hydrochloride.

Examples of an anticonvulsant include scopolamine hydrobromide.

Examples of a central nervous system drug include citicoline.

Examples of an antiepileptic agent include phenytoin.

Examples of an antihypertensive agent include carvedilol and olmesartan medoxomil.

Examples of an antihyperlipidemic agent include pravastatin sodium.

Examples of the antibiotic and antimicrobial agents include clarithromycin and levofloxacin.

Examples of an antidiabetic agent include pioglitazone hydrochloride.

Examples of an antirheumatic drug include methotrexate and bucillamine.

Examples of a hormonal agent include dexamethasone phosphate sodium.

Examples of an alkaloid narcotic include cocaine hydrochloride.

Examples of an antigout drug include colchicine.

Examples of an antineoplastic agent include 5-fluorouracil.

Examples of nutritional ingredients include proteins, sugars, lipids, vitamins, and minerals.

Examples of the vitamins include astaxanthin, vitamin A, riboflavin, ascorbic acid, and tocopherol acetate.

The excipient which can be used in combination with the porous silica particle composition of the present invention is not particularly limited and examples thereof include one or more of the aforementioned starch, adipic acid, pregelatinized starch, erythritol, sodium carboxymethyl starch, carmellose, carmellose calcium, carmellose sodium, agar, xylitol, guar gum, acrylic acid starch, L-aspartic acid, aminoethyl sulfonic acid, amino acetic acid, candy (powder), gum arabic, gum arabic powder, alginic acid, sodium alginate, pregelatinized starch, inositol, ethyl cellulose, ethylene vinyl acetate copolymer, erythritol, sodium chloride, olive oil, kaolin, cacao butter, casein, fructose, pumice particles, carmellose, carmellose sodium, dry yeast, dried aluminum hydroxide gel, dry sodium sulfate, dry magnesium sulfate, agar, agar powder, xylitol, citric acid, sodium citrate, disodium citrate, glycerin, calcium glycerophosphate, sodium gluconate, L-glutamine, clay, clay particles, croscarmellose sodium, aluminum silicate, synthetic aluminum silicate-hydroxypropyl starch-crystalline cellulose, magnesium aluminosilicate, calcium silicate, magnesium silicate, light liquid paraffin, cinnamon powder, crystalline cellulose, crystalline cellulose-carmellose sodium, crystalline cellulose fine particles, brown rice koji, synthetic aluminum silicate, synthetic hydrotalcite, sesame oil, flour, wheat starch, wheat germ flour, rice flour, rice starch, potassium acetate, calcium acetate, cellulose acetate phthalate, safflower oil, white beeswax, zinc oxide, titanium oxide, magnesium oxide, β-cyclodextrin, dihydroxyaluminum aminoacetate, 2,6-di-t-butyl-4-methylphenol, dimethylpolysiloxane, tartaric acid, potassium hydrogen tartrate, calcined gypsum, sucrose fatty acid ester, aluminum magnesium hydroxide, aluminum hydroxide gel, aluminum hydroxide-sodium bicarbonate co-precipitate, magnesium hydroxide, squalane, stearyl alcohol, stearic acid, calcium stearate, polyoxyl stearate, magnesium stearate, purified gelatin, purified shellac, purified sucrose, purified sucrose spherical granule, refined montan wax, Zein, sorbitan sesquioleate, cetanol, gypsum, cetostearyl alcohol, shellac, gelatin, sorbitan fatty acid ester, D-sorbitol, tricalcium phosphate, soybean oil, soybean oil unsaponifiable matter, soybean lecithin, skimmed milk powder, talc, ammonium carbonate, calcium carbonate, magnesium carbonate, neutral anhydrous sodium sulfate, low-substituted hydroxypropyl cellulose, dextran, dextrin, natural aluminum silicate, corn syrup, maize starch, trehalose, tragacanth, calcium lactate, lactose, hydrotalcite, maltose, white shellac, white vaseline, white clay, sucrose, sucrose starch spherical granule, hull-less barley green leaf extract powder, hull-less barley green leaf green juice dry powder, honey, palatinit, palatinose, paraffin, potato starch, semi-digested starch, human serum albumin, hydroxypropyl starch, hydroxypropyl cellulose, phytic acid, glucose, glucose hydrate, partly pregelatinized starch, pullulan, propylene glycol, powdered hydrogenated maltose starch syrup, powder cellulose, pectine, bentonite, sodium polyacrylate, polyethylene glycol, polyoxyethylene alkyl ether, polyoxyethylene hydrogenated castor oil, polyoxyethylene polyoxypropylene glycol, sodium polystyrenesulfonate, polysorbate, polyvinylacetal diethylaminoacetate, polyvinyl pyrrolidone, maltitol, maltose, D-mannitol, starch syrup, isopropyl myristate, anhydrous lactose, calcium hydrogen phosphate, calcium hydrogen phosphate granule, magnesium aluminometasilicate, methyl cellulose, cotton seed flour, cotton seed oil, Japan wax, aluminum monostearate, glycerol monostearate, sorbitan monostearate, silicic anhydride, medicinal carbon, peanut oil, aluminum sulfate, calcium sulfate, spherical limestone, spherical maize starch, liquid paraffin, dl-malic acid, calcium monohydrogen phosphate, calcium hydrogen phosphate, potassium hydrogen phosphate, and sodium hydrogen phosphate. Any of them may be used alone, or two or more thereof may be used in combination.

In the present invention, examples of the lubricant include gum arabic powder, cacao butter, carnauba wax, carmellose calcium, carmellose sodium, caropeptide, hydrated silicon dioxide, dried aluminum hydroxide gel, glycerin, magnesium silicate, light silicic anhydride, light liquid paraffin, crystalline cellulose, hardened oil, synthetic aluminum silicate, sesame oil, wheat starch, white beeswax, magnesium oxide, dimethylpolysiloxane, potassium sodium tartrate, sucrose fatty acid ester, glycerin fatty acid ester, silicone resin, aluminum hydroxide gel, stearyl alcohol, stearic acid, aluminum stearate, calcium stearate, polyoxyl stearate, magnesium stearate, cetanol, gelatin, talc, magnesium carbonate, precipitated calcium carbonate, maize starch (corn starch), lactose, hard fat, sucrose, potato starch, hydroxypropyl cellulose, fumaric acid, sodium stearyl fumarate, polyethylene glycol, polyoxyethylene polyoxypropylene glycol, polysorbate, beeswax, magnesium aluminometasilicate, methyl cellulose, Japan wax, glycerol monostearate, sodium lauryl sulfate, calcium sulfate, magnesium sulfate, liquid paraffin, and phosphoric acid.

In the present invention, a disintegrant typically used in pharmaceuticals can be used as the disintegrant, and examples thereof include one or more of adipic acid, alginic acid, sodium alginate, pregelatinized starch, erythritol, fructose, sodium carboxymethyl starch, carmellose, carmellose calcium, carmellose sodium, agar, xylitol, guar gum, calcium citrate, croscarmellose sodium, crospovidone, synthetic aluminum silicate, magnesium aluminosilicate, crystalline cellulose, crystalline cellulose-carmellose sodium, wheat starch, rice starch, cellulose acetate phthalate, dioctyl sodium sulfosuccinate, sucrose fatty acid ester, aluminum magnesium hydroxide, calcium stearate, polyoxyl stearate, sorbitan sesquioleate, gelatin, shellac, sorbitol, sorbitan fatty acid ester, talc, sodium bicarbonate, magnesium carbonate, precipitated calcium carbonate, dextrin, sodium dehydroacetate, maize starch, tragacanth, trehalose, lactose, maltose, sucrose, hydrotalcite, honey, palatinit, palatinose, potato starch, hydroxyethyl methyl cellulose, hydroxypropyl starch, hydroxypropyl cellulose, glucose, bentonite, partly pregelatinized starch, monosodium fumarate, polyethylene glycol, polyoxyethylene hydrogenated castor oil, polyoxyethylene polyoxypropylene glycol, polysorbate, polyvinylacetal diethylaminoacetate, polyvinyl pyrrolidone, maltitol, D-mannitol, anhydrous citric acid, magnesium aluminometasilicate, methyl cellulose, glycerol monostearate, sodium lauryl sulfate, and carmellose. Any of them may be used alone, or two or more thereof may be used in combination.

In the present invention, examples of the binder include one or more of alginic acid, ethyl acrylate-methyl methacrylate copolymer emulsion, acetylglycerin fatty acid ester, aminoalkyl methacrylate copolymer E, aminoalkyl methacrylate copolymer RS, aminoethyl sulfonic acid, candy (powder), gum arabic, gum arabic powder, sodium alginate, propylene glycol alginate, pregelatinized starch, ester gum H, ethyl cellulose, Phellodendron amurense powder, hydrolyzed gelatin powder, casein sodium, fructose, caramel, karaya gum powder, carboxyvinyl polymer, carboxymethyl ethyl cellulose, sodium carboxymethyl starch, carmellose, carmellose sodium, agar, kanbai powder, xanthane gum, beef tallow hardened oil, guar gum, glycerin, synthetic aluminum silicate, light silicic anhydride-containing hydroxypropyl cellulose, crystalline cellulose, hardened oil, copolyvidone, sesame oil, flour, wheat starch, rice flour, rice starch, vinyl acetate resin, cellulose acetate phthalate, white beeswax, oxidized starch, dioctyl sodium sulfosuccinate, dihydroxyaluminum aminoacetate, potassium sodium tartarate, sucrose fatty acid ester, stearyl alcohol, stearic acid, calcium stearate, polyoxyl stearate, sorbitan sesquioleate, cetanol, gelatin, shellac, sorbitan fatty acid ester, D-sorbitol, soybean lecithin, calcium carbonate, simple syrup, dextrin, starch (soluble), maize starch, tragacanth, paraffin, potato starch, hydroxyethyl cellulose, hydroxyethyl methyl cellulose, hydroxypropyl starch, hydroxypropyl cellulose, hydroxypropyl methyl cellulose, hydroxypropyl methyl cellulose acetate succinate, hydroxypropyl methyl cellulose phthalate, piperonyl butoxide, butylphthalyl butyl glycolate, glucose, partly pregelatinized starch, fumaric acid, pullulan, propylene glycol, pectine, sodium polyacrylate, partially neutralized polyacrylic acid, polyethylene glycol, polyoxyethylene polyoxypropylene glycol, polysorbate, polyvinylacetal diethylaminoacetate, polyvinyl alcohol (completely saponified matter), polyvinyl alcohol (partially saponified matter), polyvinyl pyrrolidone, polybutene, sodium polyphosphate, D-mannitol, starch syrup, and magnesium aluminometasilicate. Any of them may be used alone, or two or more thereof may be used in combination.

The porous silica particle composition of the present invention can be made into a porous silica particle composition in which the active pharmaceutical ingredient is adsorbed by adsorbing the active pharmaceutical ingredient or dissolving and adsorbing the active pharmaceutical ingredient into a liquid ingredient, followed by mixing with the porous silica particle composition and making the mixture into a powder. Examples of the adsorption method include methods of melting a solid active ingredient by heating to adsorb it, or dissolving it in a solvent for adsorption and then removing the solvent, or dissolving it in an ingestible fat and oil and the like for adsorption. When the active pharmaceutical ingredient itself is a liquid, it is not particularly required to be dissolved in a solvent and may be diluted with a solvent if necessary, and then allowed to adsorb to the porous silica particle composition of the present invention into powder. The blend ratio (weight ratio) of the silica particle composition to the active pharmaceutical ingredient in the powder thus obtained is such that 'the porous silica particle composition of the present invention': 'the active pharmaceutical ingredient'=from about 1:0.0001 to 1:10. The active pharmaceutical ingredient to be adsorbed is preferably liquid at room temperature and examples thereof include sodium valproate, tocopherol acetate, various extracts of traditional Chinese medicines, selegiline, nitroglycerin, nicotine, ciclopirox olamine, tolubuterol, propanolol, bupranolol, arecoline, methamphetamine, ethosuximide, merproic acid, prilocaine, dyclonine, and amphetaminil.

Next, a solid dispersion will be described in detail. The solid dispersion refers to one in which one or more active ingredients are dispersed in a solid-state inert carrier and/or the matrix thereof (W. L. Chiou, S. Riegelman: J. Pharm. Sci., 60, 1281, 1971). In particular, it is known that making a poorly soluble drug as a solid amorphous dispersion results in a remarkable improvement of solubility and bioavailability and the elimination of the difference between the blood concentrations on an empty and full stomach. The solid dispersion can be produced by a conventional method of producing the solid dispersion such as (1) a method of dissolving the porous silica particle composition of the present invention and the active pharmaceutical ingredient, or the porous silica particle composition of the present invention, the active ingredient, and the matrix ingredient in a solution and then removing the solvent, (2) a method of melting them by heating and then cooling, or (3) a method of mixing them and then imparting mechanical impact. The blend ratio (weight ratio) of the active pharmaceutical ingredient to the matrix ingredient may be appropriately selected from the ratio at which the active pharmaceutical ingredient can be amorphous or the range in which the active pharmaceutical ingredient is stably amorphous, and is usually in a range from 5:1 to 1:10. The blend ratio (weight ratio) of the silica particle composition to the active pharmaceutical ingredient in the solid dispersion is in a range such that 'the porous silica particle composition of the present invention': 'the active pharmaceutical ingredient'=from 1:0.0001 to 1:10. It is preferable that the blend ratio (weight ratio) of 'the porous silica particle composition of the present invention' to 'the active pharmaceutical ingredient and matrix ingredient' in the solid dispersion be usually in a range such that 'the porous silica of the present invention': 'the active pharmaceutical ingredient+matrix ingredient'=from 1:0.0001 to 1:100.

Here, the active pharmaceutical ingredient applicable to the solid dispersion is one which is usually poorly soluble, and examples thereof include indometacin, itraconazole, nifedipine, ketoprofen, flurbiprofen, loxoprofen, ketorolac, felbinac, diclofenac, salicylic acid, glycol salicylate, acetyl salicylate, flufenamic acid, mefenamic acid, acemetacin, alclofenac, ibuprofen, sulindac, tolmetin, lobenzarit, penicillamine, oxaprozin, diflunisal, fenbufen, fentiazac, naproxen, pranoprofen, tiaprofen, suprofen, oxaprozin, etodolac, zaltofen, telmisartan, ursodeoxycholic acid, maprotiline hydrochloride, papaverine hydrochloride, norepinephrine, berberine chloride, cetraxate hydrochloride, sulfamethoxazole, metronidazole, diazepam, cimetidine, famotidine, bromhexine hydrochloride, difenidol hydrochloride, caffeine, digoxin, verapamil hydrochloride, erythromycin, clarithromycin, kitasamycin, josamycin, roxithromycin, and midecamycin.

Examples of the matrix ingredient applicable to the solid dispersion include hypromellose, hydroxypropyl cellulose, methyl cellulose, hydroxypropyl methyl cellulose acetate succinate, hydroxypropyl methyl cellulose phthalate, cellulose acetate phthalate, polyvinyl pyrrolidone, polyethylene glycol, polyvinyl pyrrolidone copolymer, and methacrylic acid copolymer. These matrix ingredients can be used in combination of two or more, and may be appropriately used in combination, in accordance with the kind of the active pharmaceutical ingredient, the method for use, and the like.

Regarding the shape of the porous silica particle composition of the present invention used for the solid dispersion, a spherical one having an average particle diameter from 10 to 150 μm or a non-spherical one having an average particle diameter from 1 to 40 μm can be used, and it can be appropriately selected in accordance with the properties of the drug and the desired physical properties of the solid dispersion. For example, when the active pharmaceutical ingredient is desired to be held in the void of the porous silica particle composition of the present invention, the spherical one is preferably used. When a solid dispersion made of fine powder of a drug and the porous silica particle composition of the present invention is desired, the non-spherical one is preferably used.

In addition to the porous silica particle composition of the present invention, the active ingredient, and the matrix ingredient, ingredients which can be added upon granulation of pharmaceuticals, such as a surfactant, a binder, and a fluidizer can be blended into the solid dispersion. This is for the same purpose as the conventional granulation process, for example, for improvement of the wetting properties of the solid dispersion, or for the production process.

Next, a bitterness-masking particle composition will be described in detail. This masking particle composition may be composed of the porous silica particle composition of the present invention, a bitter drug, and if necessary, a polymer. Examples of the particle structure of the bitterness-masking particle composition include (1) a structure in which the porous silica particle composition of the present invention adsorbed with the drug is coated with the polymer, (2) a structure of the porous silica particle composition of the present invention adsorbed with the polymer containing the drug, or (3) a structure having both of them. Examples thereof also include agglomerated particles and granulated particles having these (1) to (3) structures.

Herein, bitterness masking refers that bitterness of bitter ingredients is not felt after the bitterness-masking particle composition or a pharmaceutical composition containing an active ingredient is disintegrated by buccal administration or in the buccal cavity and until it is swallowed, and that bitterness is not felt for at least 30 seconds, and preferably for 60 seconds.

Note that the bitter drug is used in the same meaning as the active ingredient having bitterness in the present invention.

The polymer to be used in the bitterness masking in the present invention is not particularly limited, as long as it is a pharmacologically acceptable polymer, and examples thereof include a water soluble polymer and water insoluble polymer. In the present invention, the "water insoluble polymer" refers to a polymer having a water solubility at 20° C. of less than 10 g/L.

Examples of the water soluble polymer include water soluble cellulose derivatives, water soluble vinyl polymer derivatives, water soluble acrylic acid copolymer, and polyhydric alcohol polymer. Examples of the water insoluble polymer include water insoluble cellulose ether and water insoluble acrylic acid copolymer.

Examples of the polymer include ethyl acrylate-methyl methacrylate copolymer, methyl acrylate-methacrylate copolymer, methacrylic acid copolymer L, methacrylic acid copolymer LD, methacrylic acid copolymer S, aminoacryl methacrylate copolymer E, aminoacryl methacrylate copolymer RS, dimethylaminoethyl methacrylate-methyl methacrylate copolymer, ethyl cellulose, hydroxypropyl cellulose, hydroxypropyl methyl cellulose, hydroxypropyl methyl cellulose phthalate, hydroxypropyl methyl cellulose succinate, hydroxypropyl methyl cellulose acetate succinate, methyl cellulose, carboxymethyl ethyl cellulose, sodium carboxymethyl cellulose, acetyl cellulose, cellulose acetate phthalate, polyvinyl pyrrolidone, and polyvinylacetal diethylaminoacetate.

Among them, preferable examples thereof include ethyl acrylate-methyl methacrylate copolymer, methyl acrylate-methacrylate copolymer, methacrylic acid copolymer L, methacrylic acid copolymer LD, methacrylic acid copolymer S, aminoacryl methacrylate copolymer E, aminoacryl methacrylate copolymer RS, dimethylaminoethyl methacrylate-methyl methacrylate copolymer, ethyl cellulose, hydroxypropyl cellulose, hydroxypropyl methyl cellulose, hydroxypropyl methyl cellulose phthalate, hydroxypropyl methyl cellulose succinate, hydroxypropyl methyl cellulose acetate succinate, methyl cellulose, carboxymethyl ethyl cellulose, and sodium carboxymethyl cellulose, and more preferable examples thereof include ethyl acrylate-methyl methacrylate copolymer, aminoacryl methacrylate copolymer E, and ethyl cellulose.

In the bitterness-masking particle composition of the present invention, a plasticizer such as triethyl citrate, polyethylene glycol 400 to 6,000, and polysorbate 80, and a lubricant such as talc, glycerol monostearate, and magnesium stearate may be blended to have better film forming properties of the polymer to be used.

The blend ratio of the bitterness-masking particle composition of the present invention in which the drug and the polymer are contained in the porous silica particle composition of the present invention is shown below.

The blend ratio of the drug to the polymer is such that preferably drug:polymer=from 10:1 to 1:10, more preferably drug:polymer=from 3:1 to 1:4, further preferably drug:polymer=from 2:1 to 1:3, and even more preferably drug:polymer=from 2:1 to 1:2.

The blend ratio of silica to the total amount of the drug and polymer is preferably (drug+polymer):silica=from 4:1 to 1:100, more preferably (drug+polymer):silica=from 3:1 to 1:10, and further preferably (drug+polymer):silica from 2:1 to 1:4.

The blend ratio of the particle composition of the present invention in which the drug contained in the silica is coated with the polymer is shown below.

The blend ratio of the drug and silica is preferably drug:silica=from 2:1 to 1:4, more preferably drug:silica=from 1:1 to 1:3, and further preferably drug:silica=from 1:1 to 1:2.

The blend ratio of the silica and polymer is preferably silica:polymer=from 5:1 to 1:5, more preferably silica:polymer=from 3:1 to 1:3, and further preferably silica:polymer=from 2:1 to 1:2.

The blend ratio of the drug, polymer, and silica can be appropriately selected in accordance with the intensity of the bitterness of the drug, the particle diameter of the drug, the method for producing the particle composition of the present invention, and the desired size of the particle composition of the present invention.

The bitter drug used in the present invention is a generic term for the drug having unpleasant tastes such as bitterness and sourness and may be either water soluble or poorly soluble. Specific examples thereof include acetaminophen, anhydrous caffeine, clemastine fumarate, promethazine hydrochloride, mequitazine, diphenhydramine hydrochloride, epinastine hydrochloride, dl-chlorpheniramine maleate, phenylephrine hydrochloride, methylephedrine hydrochloride, ephedrine hydrochloride, dextromethorphan, noscapine hydrochloride, methylephedrine hydrochloride, bromhexine hydrochloride, salicylamide, ibuprofen, phenacetin, diclofenac sodium, mosapride citrate, quinine, digitalis, berberine chloride, meclofenoxate hydrochloride, etilefrine hydrochloride, trihexyphenidyl hydrochloride, and enoxacin.

To ease the production process, ingredients for uniformization, fluidization, preventing agglomeration, and the like can be blended into the bitterness-masking particle composition of the present invention. Examples of the ingredients for uniformization, fluidization, preventing agglomeration, and the like include talc, crystalline cellulose, starch, hydrated silicon dioxide, light silicic anhydride, sodium stearyl fumarate, magnesium stearate, calcium stearate, titanium oxide, magnesium aluminometasilicate, and calcium hydrogen phosphate.

To modify the surface state of the bitterness-masking particle composition of the present invention to desired physical properties, a surface modifying material can be coated or attached to the particle surface. Examples of the surface modifying material include not only common sugar alcohols such as mannitol, xylitol, and erythritol, but also lactose hydrate and sucrose.

Hereinafter, a method of producing the bitterness-masking particle composition in which the surface of the drug contained in the silica is coated with the polymer will be described.

As a granulation method of the particles, methods used in a granulation process for forming a usual drug coating layer can be used, and examples thereof include a stirring granulation method, a fluidized bed granulation method, a rolling granulation method, a spray drying fluidized bed granulation method, and an extrusion granulation method. The stirring granulation method, the fluidized bed granulation method, and the rolling granulation method are preferable.

In the production of the particle composition of the present invention by the stirring granulation method, a dissolution/suspension of the drug and a solution/suspension of the polymer are prepared in advance. While stirring silicon dioxide in a tank of a stirring granulator, the aforementioned dissolution/suspension of the drug is added thereto and stirred, and then the aforementioned solution/suspension of the polymer is added thereto to granulate. In addition, when drying is carried out between the addition of the dissolution/suspension of the drug and the addition of the solution/suspension of the polymer, the bitterness-masking effect can be more enhanced. If necessary, the ingredients for uniformization, fluidization, preventing agglomeration, and the like can be added. After the granulation, secondary drying in accordance with the ordinary method and then sizing can be carried out. If the amount of the drug solution or the viscosity of the solution prevents from granulation by adding the drug solution and the polymer solution in one portion due to, granulation and drying can be repeated multiple times in accordance with the amount of the drug solution or the amount of the polymer solution. The method of adding the solution may be carried out by dropping or spraying. The temperature at the time of stirring granulation can be room temperature, for example, from 10 to 40° C., and when it is desired to remove some water during stirring granulation, the temperature may be increased from about 40 to 90° C.

The amount of the drug solution to be added in relation to silica is preferably in a range of silica (g):drug solution (g)=from 100:1 to 1:8, more preferably in a range of silica:drug solution=from 50:1 to 1:5, and further preferably in a range of silica:drug solution=from 10:1 to 1:5.

The amount of the polymer solution to be added in relation to silica is preferably in a range of silica (g):polymer solution (g)=from 2:1 to 1:8, more preferably in a range of silica:polymer solution=from 1:2 to 1:5, and further preferably in a range of silica:polymer solution=from 1:3 to 1:4.

The total liquid amount of the drug solution and the polymer solution in relation to silica is preferably in a range such that the total solution amount (g)/silica (g) is 9 or less, more preferably in a range such that the total solution amount/silica is 6 or less, and further preferably in a range that the total solution amount/silica is 6 or less.

The total amount of the drug solution and the polymer solution to be added at this time is an amount addible in one stirring granulation step. When stirring granulation is carried out again after drying and removal of the solvent are performed, the same amount of solution can be added, and the same applies to the case where stirring granulation is repeated multiple times.

In the production of the particle composition of the present invention by the fluidized bed granulation method, granulation may be carried out by spraying the drug solution while fluidizing silica in the fluidized bed, and then spraying the polymer solution. If necessary, for the purpose of homogenization, ingredients for homogenization, fluidization, preventing agglomeration, and the like can be blended to the aforementioned solution, or the solution of the ingredients can be separately sprayed thereto. The temperature, the amount of airflow, the solution concentration, and the solution addition rate may be set in accordance with the desired ingredient, and it may be carried out in accordance with the conventional method of fluidized bed granulation.

In the production of the particle composition of the present invention by the rolling granulation method, granulation may be carried out by spraying the drug solution while rolling silica, and then spraying the polymer solution. If necessary, the ingredients for uniformization, fluidization, preventing agglomeration, and the like can be blended to the aforementioned solution, or the solution of the ingredients can be separately sprayed thereto. The temperature, the amount of airflow, the solution concentration, and the solution addition rate may be set in accordance with the desired ingredient, and it may be carried out in accordance with the conventional method of fluidized bed granulation.

In case further drying is required after granulation, drying can be carried out by using a usual drying method such as shelf drying and fluidized bed drying so that the desired water content can be obtained. The particle diameter can be modulated by carrying out sizing or cracking after drying.

Hereinafter, a method of producing the bitterness-masking particle composition of the present invention containing the drug and the polymer in silica will be described.

As a granulation method of the particles, a method used in a granulation step where the drug is usually allowed to contain can be used, and examples thereof include the stirring granulation method, the fluidized bed granulation method, the rolling granulation method, the spray drying fluidized bed granulation method, and the extrusion granulation method. The fluidized bed granulation method, the rolling granulation method, and the stirring granulation method are preferable.

In the production of the bitterness-masking particle composition of the present invention by the fluidized bed granulation method, granulation may be carried out by spraying the dissolution and/or suspension of the drug and the polymer while fluidizing silica in the fluidized bed. If necessary, the ingredients for uniformization, fluidization, preventing agglomeration, and the like can be blended or separately sprayed thereto. The temperature, the amount of airflow, and the solution addition rate may be set in accordance with the desired ingredient, and it may be carried out in accordance with the conventional method of fluidized bed granulation.

In the production of the bitterness-masking particle composition of the present invention by a rolling fluidized bed granulation method, granulation may be carried out by spraying the drug and polymer solutions while rolling silica. If necessary, the ingredients for uniformization, fluidization, preventing agglomeration, and the like can be added thereto. The temperature and the spray rate may be set in accordance with the desired ingredient, and it may be carried out in accordance with the conventional method of rolling fluidized bed granulation.

In the production of the bitterness-masking particle composition of the present invention by a spray drying method, spraying and granulation may be carried out after preparing the silica, drug, and polymer solutions. If necessary, ingredients for uniformization, fluidization, and the like can be added thereto. The solution concentration, the temperature, and the spray rate may be set in accordance with the desired ingredient, and it may be carried out in accordance with the conventional method of spray drying.

In the production of the particle composition of the present invention by the stirring granulation method, a solution/suspension of the drug and the polymer may be added while stirring silica in a tank of a stirring granulator, and then granulation may be carried out. It can be sized to the desired particle diameter by drying after granulation. If granulation is not to be carried out due to too much amount of the drug and polymer solution, or granulation is not to be carried out due to the viscosity of the solution, granulation and drying can be repeated multiple times in accordance with the amount of the drug contained. The method of adding the solution may be carried out by dropping or spraying. The temperature at the time of stirring granulation can be room temperature of from 10 to 40° C., and when it is desired to remove some water during stirring granulation, the temperature may be increased to from about 40 to 80° C.

In case further drying is required after granulation, drying can be carried out by using a usual drying method such as shelf drying and fluidized bed drying so that the desired water content can be obtained. The particle diameter can be modulated by carrying out sizing or cracking after drying.

In the production method of the particle composition of the present invention, the drug solution, the polymer solution, or the mixed solution of the drug and the polymer may be either a state where the drug or the polymer is dissolved or a state where the drug or the polymer is dispersed/suspended.

After the active pharmaceutical ingredient is adsorbed to the porous silica particle composition of the present invention, coating may be carried out, to impart dissolution control such as enteric coating in addition to the bitterness masking. Regarding the coating method, the production apparatus is not limited, and a fluidized bed granulator, a rolling fluidized bed granulator, a centrifugal rolling fluidized bed granulator, or the like can be used. Examples of the coating ingredient include regular coating agents such as ethyl acrylate-methyl methacrylate copolymer, ethyl cellulose, hydroxypropyl cellulose, hydroxypropyl methyl cellulose, hydroxypropyl methyl cellulose phthalate, hydroxypropyl methyl cellulose succinate, hydroxypropyl methyl cellulose acetate succinate, carboxymethyl ethyl cellulose, methyl cellulose, sodium carboxymethyl cellulose, polyvinyl pyrrolidone, polyvinylacetal diethylaminoacetate, aminoacryl methacrylate copolymer-E, aminoacryl methacrylate copolymer-RS, methacrylic acid copolymer-L, methacrylic acid copolymer-LD, and methacrylic acid copolymer-S, and these coating agents can be used in combination of two or more. Further, the amount of the coating agent used may be determined in accordance with the intended purpose, such as the control of the dissolution time. For example, the film thickness can be adjusted by modulating the amount used, thereby adjusting the dissolution time.

When the porous silica particle composition of the present invention is molded into a tablet as described above, a decrease in tablet hardness can be suppressed, tablet strength can be maintained, and further the disintegration time of the tablet can be shortened. Regarding the amount thereof blended into the tablet (weight ratio), it may be blended in a ratio from about 0.1 to 10% to maintain tablet strength, and from about 0.1 to 10% to shorten disintegration time.

In the field of health food and supplement, main ingredients such as vitamin, amino acid, sugar, protein, and fat, regular health foods, additive for supplement and the porous silica particle composition of the present invention can be mixed and formulated in the same manner as for tablets, powders, granules, or capsules of the aforementioned pharmaceuticals, so that a conventional formulation of the desired health food and supplement can be obtained. Also in the field of cosmetic products, cosmetic active ingredients which can be typically used and cosmetic additives which can be typically used and the porous silica particle composition of the present invention mixed and formulated by using a conventional method of producing a cosmetic product, so that the cosmetic product such as lotion, gel, and powder can be produced in accordance with the intended purpose.

One of the features of the porous silica particles of the present invention is to have further excellent compression moldability than that of conventional silica used for the excipient. The conventional silica has a lower compression moldability than other excipients and silica alone is not tabletable. When the conventional silica is mixed with other pharmaceutical additives and tableted, it has properties of likely causing a decrease in compression moldability. Specifically, such properties can be measured and confirmed by the following evaluation methods. One method is to evaluate whether the porous silica particle composition is tabletable without tableting problems when it is tableted alone (the method of testing moldability A mentioned below). Another method is to evaluate whether the porous silica particle composition is mixed with lactose is tabletable without tableting problems when it is mixed with lactose and then tableted (the method of testing moldability B/C mentioned below). Specific conditions will be shown in Examples mentioned below.

EXAMPLES

Hereinafter, the present invention will be described by way of Examples, but the present invention is not limited thereto.

Evaluation for the sample obtained in Examples was carried out by the following methods.

[Average Particle Diameter]

The average particle diameter was measured by using a laser diffraction/scattering type particle size distribution analyzer MT3300EXII manufactured by MicrotracBEL Corp. and analyzed by using DMS2 Ver1.1.0-257F2 manufactured by MicrotracBEL Corp. For measurement conditions, the particle transparency was transparent, the particle refractive index was 1.50, the particle shape was non-spherical, the solvent was nitrogen, and the solvent refractive index was 1.00.

[BET Specific Surface Area, Pore Volume, Relative Width of Pore Size Distribution]

The BET specific surface area and the pore volume were calculated by measuring nitrogen adsorption isotherm by BELSORP-minill manufactured by MicrotracBEL Corp. and analyzing by BELMaster Ver6.3.2.1. Specifically, the specific surface area was calculated by using a BET multi-point method from the amount of nitrogen adsorption by selecting five or more consecutive points having good linearity. For the pore size distribution, a value at a relative pressure $P/P_0$=from 0.385 to 0.990 was employed and the pore distribution curve, the mode diameter, and the pore volume were determined by the BJH method. The relative width of the pore size distribution ($\gamma$) was determined as follows. The vertical axis of the pore distribution curve was taken as the volume distribution to determine the mode diameter (Dm). The shortest pore diameter (Ds) and the largest pore diameter (Dl) which correspond to the half value of the volume distribution value of the mode diameter were determined. Then, the difference between the largest pore diameter and the shortest pore diameter was divided by the volume distribution value of the mode diameter ($V_{max}$). The equation was illustrated in Expression (1) and a calculation method was illustrated in FIG. 1.

$$\gamma(\text{nm}) = \frac{D_l - D_s}{V\max} \quad \text{[Expression 1]}$$

[Oil Absorption Capacity]

The oil absorption capacity was measured by using JIS K5101-13-2 Part 13: Oil Absorption Amount—Section 1: Boiled Linseed Oil Method.

[Water Absorption Capacity]

The water absorption capacity was measured by using water instead of the boiled linseed oil based on the above oil absorption capacity test.

[Moldability]

Tableting was performed by using an φ11.3 standard flat punch by a compression moldability measurement and evaluation apparatus TAB FLEX manufactured by OKADA SEIKO CO., LTD., and the hardness of the obtained tablet was measured by using a load cell type tablet hardness tester PC-30 manufactured by OKADA SEIKO CO., LTD. and compared. Moldability A: Magnesium stearate was thinly applied to the surface of the upper punch and the lower die, 200 mg of the sample of interest was weighed, charged into the die, and compression molded under a predetermined molding pressure of 5 kN in one Cycle operation mode to obtain a tablet, followed by the measurement of hardness. Moldability B: In consideration of formulation, 90 wt % of 100 M lactose (manufactured by DMV-Fronterra Excipients GmbH & Co. KG) was mixed with 10 wt % of the sample of interest to prepare a tableting powder, magnesium stearate was thinly applied to the surface of the upper punch and the lower die, 500 mg of the tableting powder was weighed, charged into the die, and compression molded under a predetermined molding pressure of 10 kN in one Cycle operation mode to obtain a tablet, followed by the measurement of hardness.
Moldability C: Compression molding was carried out in the same manner as the formulation method of Moldability B except that 100 M lactose was replaced with FlowLac 100 (manufactured by Meggle Japan Co., Ltd.) to obtain a tablet, followed by the measurement of hardness.

[Particle Shape]

For the particle shape, a scanning electron microscope S-3000N manufactured by Hitachi High-Technologies Corporation was used to observe a secondary electron image of the particles. The long diameter and the short diameter of the porous silica particles of the present invention were measured from an SEM photograph by using an image analysis software ImageJ (developed by Wayne Rasband). The sphericity was determined by dividing the short diameter by the long diameter.

For the surface state of particles, a strongly excited conical lens FE SEM JSM-6700F manufactured by JEOL Ltd. was used to observe the surface of a secondary electron image. The length of the planar diameter of plate-like particles, thickness, and diameter of spherical particles was measured from an SEM photograph of the surface of the porous silica particles of the present invention.

[Crystallinity]

The crystallinity was measured by using an X-ray diffraction apparatus D8 ADVANCE manufactured by Bruker AXS and since there was no peak derived from a crystal in the chart, it was confirmed to be amorphous. For the measurement conditions, 2θ was ranged from 5° to 40°, Cu was used as an X-ray source, the output to be used was 40 kV-40 mA by the Bragg-Brebtano focusing geometry, LYNXEYE XE was used as a detector, and the measurement was carried out on a rotating sample stage.

Example 1

44.84 g of calcium chloride (manufactured by Wako Pure Chemical Industries, Ltd.) dissolved in 800 mL of water was added to a solution of 22.72 g of caustic soda (manufactured by Wako Pure Chemical Industries, Ltd.) in 3 L of water. To this solution was added 82.72 g of No. 3 soda silicate (manufactured by HOKURIKU KASEI INDUSTRY CO., Ltd.) in 200 mL of water and then the temperature of the mixture was raised to 40° C. Thereto was added 330.9 g of No. 3 soda silicate dissolved in 800 mL of water. Thereto was added a diluted solution of 350.94 g of concentrated nitric acid in 280.8 mL of water, and the temperature of the mixture was raised to 70° C., and the mixture was held for one hour and cooled to room temperature to obtain a white suspension. This suspension was filtered and the residue was washed with water to obtain a white cake. This cake was suspended in water and subjected to spray drying (a spray dryer L-8 type, manufactured by OHKAWARA KAKOHKI CO., LTD.) under the conditions of a heat input of 180° C., an exhaust heat of 120° C., and a number of rotation of an atomizer of 25,000 rpm to obtain a white powder of silica.

Example 2

16.82 g of calcium chloride dissolved in 240 mL of water was added to a solution of 8.52 g of caustic soda in 900 mL of water. To this solution was added 41.11 g of No. 3 soda silicate dissolved in 60 mL of water and then the temperature of the mixture was raised to 40° C. Thereto was added 124.43 g of No. 3 soda silicate dissolved in 240 mL of water. Thereto was added a solution of 105.02 g of concentrated nitric acid in 90 mL of water, and the temperature of the mixture was raised to 70° C., and the mixture was held for one hour and cooled to room temperature to obtain a white suspension. This suspension was filtered and the residue was washed with water to obtain a white cake. Water was added to this cake to prepare a suspension, and this was subjected to spray drying (a spray dryer L-8 type, manufactured by OHKAWARA KAKOHKI CO., LTD.) under the conditions of a heat input of 180° C., an exhaust heat of 120° C., and a number of rotation of an atomizer of 25,000 rpm to obtain a white powder of silica.

Example 3

23.54 g of calcium chloride dissolved in 280 mL of water was added to a solution of 11.92 g of caustic soda in 1,050 mL of water. To this solution was added 43.55 g of No. 3 soda silicate dissolved in 70 mL of water and then the temperature of the mixture was raised to 40° C. Thereto was added 174.21 g of No. 3 soda silicate dissolved in 280 mL of water. Thereto was added a solution of 147.02 g of concentrated nitric acid in 120 mL of water, and the temperature of the mixture was raised to 70° C., and the mixture was held for one hour, and cooled to room temperature to obtain a white suspension. This suspension was filtered and the residue was washed with water to obtain a white cake. Water was added to this cake to prepare a suspension, and this was subjected to spray drying (a spray dryer L-8 type, manufactured by OHKAWARA KAKOHKI CO., LTD.) under the conditions of a heat input of 180° C., an exhaust heat of 120° C., and a number of rotation of an atomizer of 25,000 rpm to obtain a white powder of silica.

Example 4

479.0 g of calcium nitrate (manufactured by YONEYAMA CHEMICAL INDUSTRY CO., LTD.) was dissolved in water to prepare 3,000 mL of solution and added to 16,000 mL of a solution which was prepared by dissolving 113.7 g of caustic soda in water. To this solution, a solution prepared by diluting 408.6 g of No. 3 soda silicate with 600 mL of water was added and then the temperature was raised to 70° C. Thereafter, a solution prepared by diluting 1,634.3 g of No. 3 soda silicate with 2,400 L of water was added thereto. To this solution, a solution obtained by diluting 933.5 g of concentrated nitric acid with 760 mL of water was added to obtain a white suspension. This suspension was cooled, and then filtered and the residue was washed with water to obtain a white cake. Water was added to this cake to prepare a suspension having a solid content of 7.5%, and pulverized by a wet pulverizer (T.K. Mycolloider M type, manufactured by Tokushu Kika Kogyo Co., Ltd.) under the conditions of an index of 1.0. This suspension was subjected to spray drying (a spray dryer L-8 type, manufactured by OHKAWARA KAKOHKI CO., LTD.) with an atomizer under the conditions of a heat input of 180° C. and an exhaust heat of 120° C. to obtain a white powder of silica.

Example 5

146.3 g of calcium hydroxide (manufactured by Okayama Kyodo Lime Co., Ltd.) was suspended in 21 L of water for digestion, and the mixture was added to 153 mL of a solution of 189.5 g of concentrated nitric acid in water. To this solution was added 1.5 L of a solution of 415.9 g of No. 3 soda silicate in water, and then the temperature of the mixture was raised to 70° C. Thereafter, thereto was added 2 L of a solution of 1,663.7 g of No. 3 soda silicate in water and then the temperature of the mixture was raised to 80° C. To this solution, was added 1.38 L of a solution of 1,705.5 g of concentrated nitric acid in water and the mixture was held for one hour to obtain a white suspension. This suspension was cooled, and then the residue was filtered, and washed with water to obtain a white cake. Water was added to this cake to prepare a suspension, which in turn was treated with a wet fine pulverizing apparatus (Star Burst Mini, manufactured by SUGINO MACHINE LIMITED) under the conditions of the injection pressure of 200 MPa. This was subjected to spray drying (a spray dryer L-8 type, manufactured by OHKAWARA KAKOHKI CO., LTD.) under the conditions of a heat input of 180° C., an exhaust heat of 120° C., and a number of rotation of an atomizer of 25,000 rpm to obtain a white powder of silica.

Example 6

Figure 2:
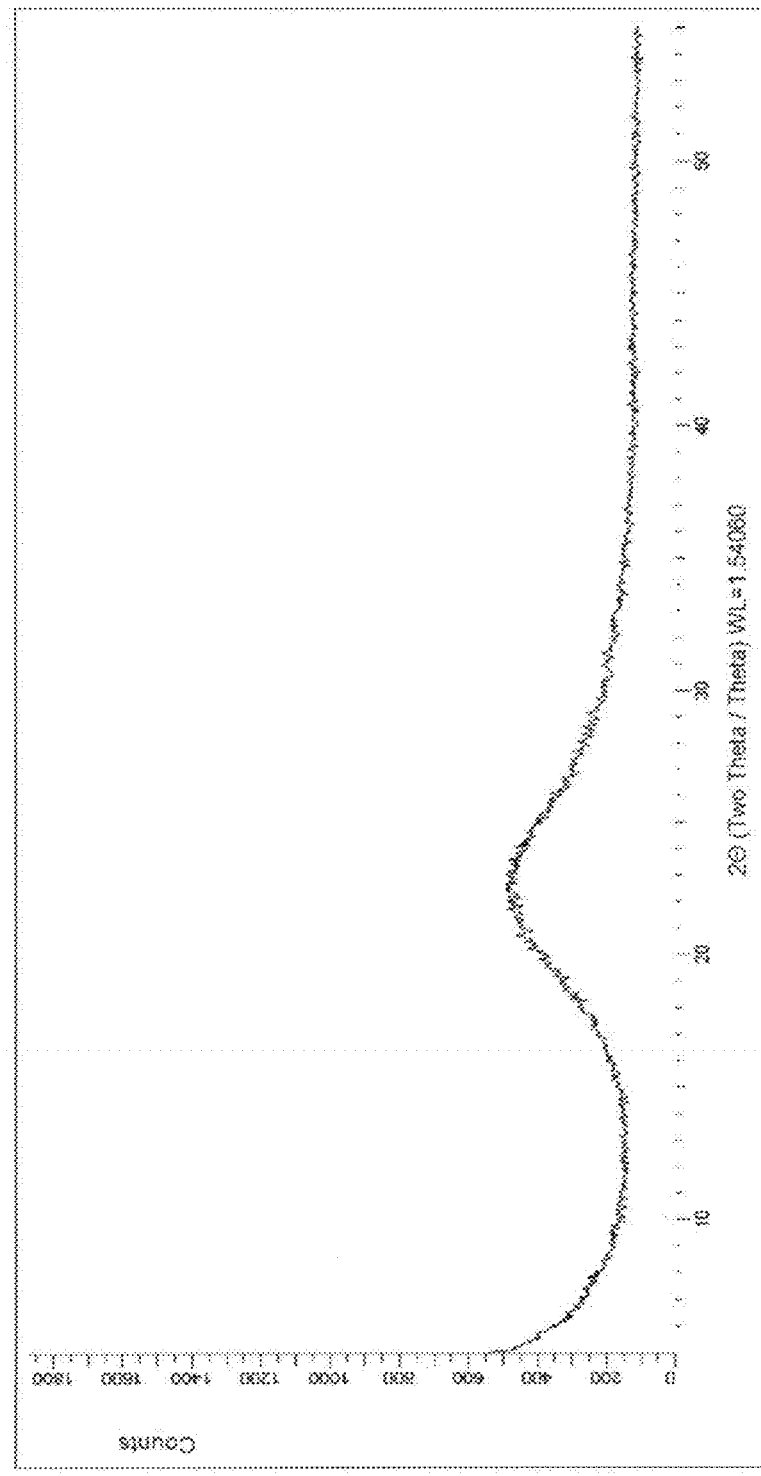
FIG. 2 is an XRD chart of the porous amorphous silica of Example 6.
Figure 3:
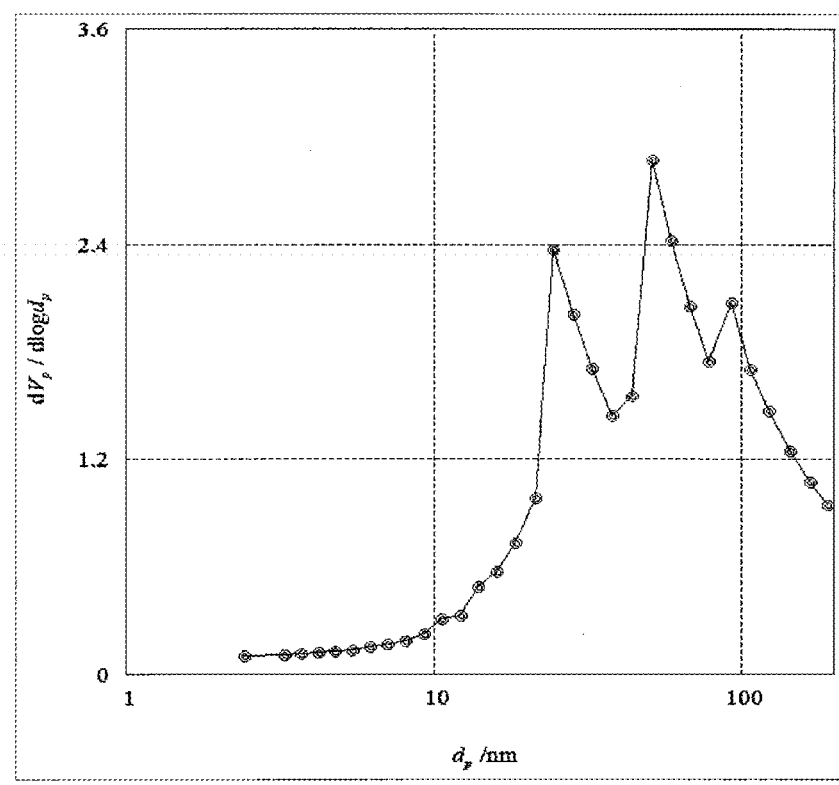
FIG. 3 is a pore size distribution chart of the porous amorphous silica of Example 6 obtained by the BJH method.
Figure 4:
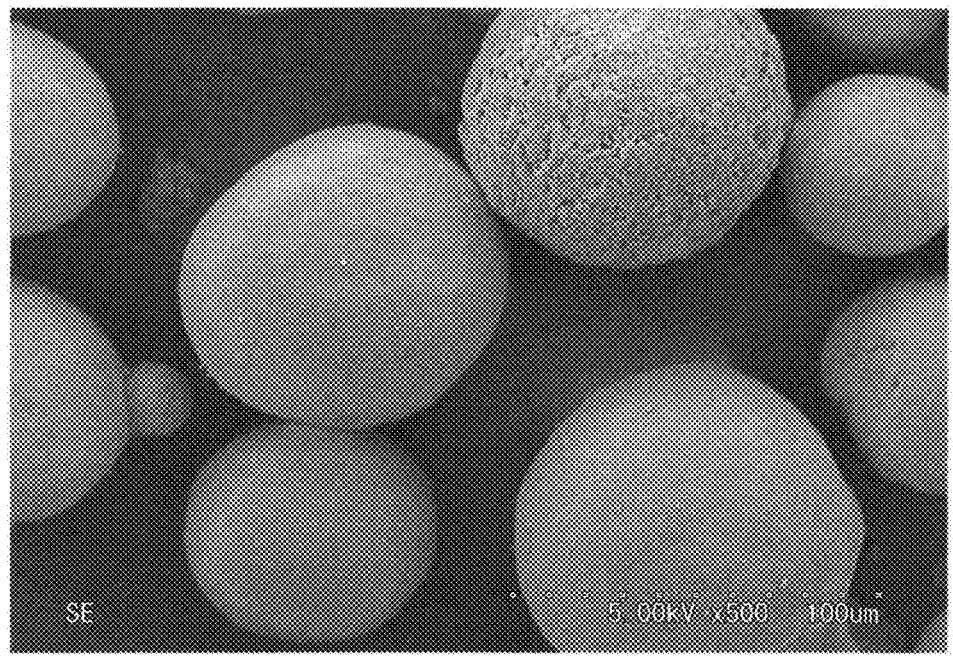
FIG. 4 is an SEM photograph (500 times) of the porous amorphous silica of Example 6.
Figure 5:
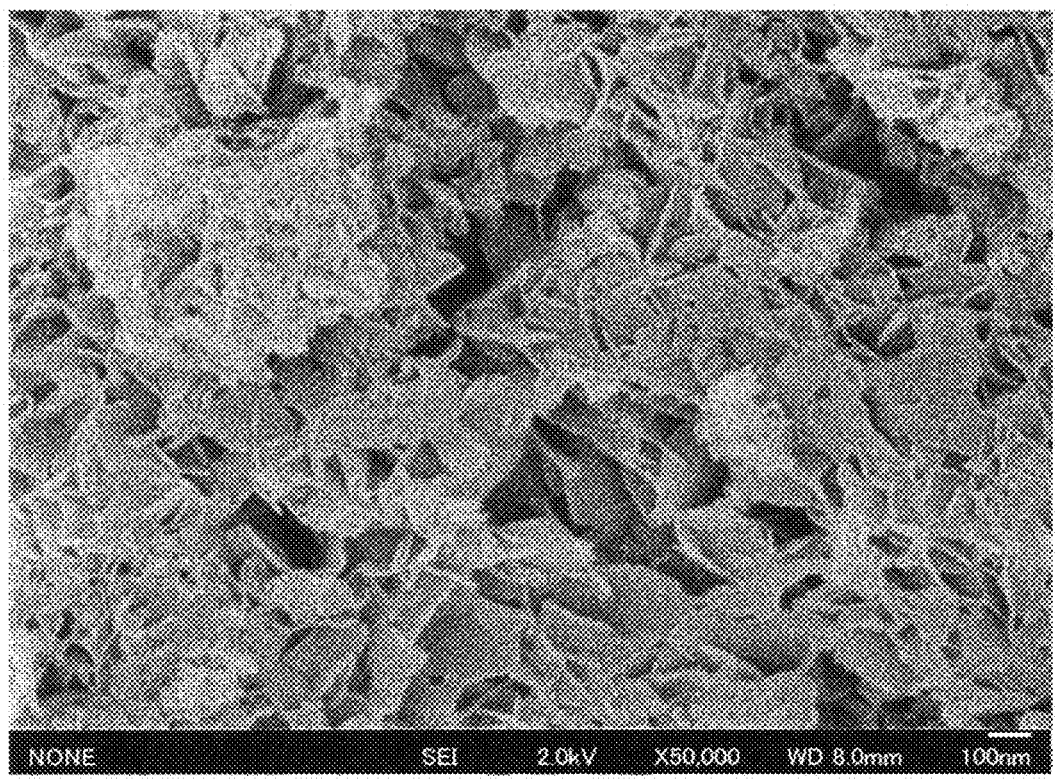
FIG. 5 is an FE-SEM photograph (50,000 times) of the porous amorphous silica of Example 6.

To 20,000 L of quicklime solution having a calcium concentration of 0.38%, a solution of 188 kg of 39.5% nitric acid in 152 L of water was added. To this solution was added a solution of 410 kg of No. 3 soda silicate in 1,500 L of water. The temperature of the mixture was raised to 60° C., and thereto was added a solution of 1,640 kg of No. 3 soda silicate in 2,000 L of water. Subsequently, thereto was added a solution of 1,700 kg of 39.5% nitric acid in 1,400 L of water, and then, the mixture was cooled to room temperature to obtain a suspension. After this suspension was washed with water by decantation until it became neutral, this suspension was treated with a wet fine pulverizing apparatus (Star Burst 100 HJP-25080, manufactured by SUGINO MACHINE LIMITED) under the conditions of the injection pressure of 100 MPa. This suspension was subjected to spray drying (S-160N/R type, manufactured by Ashizawa Nitro Atomizer Co., Ltd.) with an atomizer under the conditions of a heat input of 310° C. and an exhaust heat of 150° C. to obtain amorphous silica white powder having a good flowability. The water content of the obtained silica powder, that is, the loss on drying was 2.3%, and the loss on ignition was 5.0%. The silicon dioxide content of the silica powder was 99.3%, the sphericity was 0.93, and an XRD chart (FIG. 2) showed a halo pattern.

Example 7

10 g of the amorphous silica powder obtained in Example 6 was pulverized with a jet mill (single track jet mill STJ-200, manufactured by SEISHIN ENTERPRISE Co., Ltd.) under the conditions of a P pressure of 0.7 MPa and a G pressure of 0.4 MPa to obtain 9.8 kg of amorphous silica white powder.

Example 8

208.8 g of the suspension treated with the wet fine pulverizing apparatus in Example 6 was divided into six centrifuge tubes, and about 20 g of acetone was added thereto and well stirred, and then the mixture was subjected to centrifugation to remove the supernatant. Then, acetone was added such that the total content of each centrifuge tube could be about 35 g and the mixture was shaken vigorously and subjected to centrifugation to remove the supernatant. This operation was repeated three times. Thereafter, acetone was added thereto so that the slurry solid content could be about 10% and the mixture was spread on a tray and air dried for 10 days, and then vacuum dried for 17 hours and sieved with a sieve of 20 mesh to obtain about 6 g of amorphous silica white powder.

Comparative Examples 1 to 6

Comparative Example 1 used Adsolider 101 (product name, manufactured by Freund Corporation)
Comparative Example 2 used Syloid 244FP (product name, manufactured by W.R.Grace and Company)
Comparative Example 3 used Syloid XDP 3050 (product name, manufactured by W.R.Grace and Company)
Comparative Example 4 used Partech SLC (product name, manufactured by Merck KGaA)
Comparative Example 5 used Aeroperl 300 (product name, manufactured by Evonik Industries AG)
Comparative Example 6 used Aerosil 200 (product name, manufactured by NIPPON AEROSIL CO., LTD.).

TABLE 1

| | Example 1 | Example 2 | Example 3 | Example 4 | Example 5 | Example 6 |
|---|---|---|---|---|---|---|
| Oil absorption capacity [mL/g] | 4.8 | 3.7 | 3.1 | 5.0 | 3.24 | 3.40 |
| Static specific volume [mL/g] | 9.9 | 8.6 | 8.6 | 9.17 | 6.94 | 6.15 |
| Dynamic specific volume [mL/g] | 7.4 | 6.1 | 6.1 | 6.43 | 5.30 | 4.92 |
| Average particle diameter [μm] | 32.6 | 33.7 | 32.0 | 28.5 | 31.1 | 69.76 |
| BET specific surface area [m$^2$/g] | 674 | 570 | 547 | 467 | 467 | 361 |
| Pore volume [cm$^2$/g] | 1.90 | 1.41 | 1.12 | 2.08 | 2.32 | 1.99 |

TABLE 1-continued

|  | Example 1 | Example 2 | Example 3 | Example 4 | Example 5 | Example 6 |
|---|---|---|---|---|---|---|
| Pore mode diameter [nm] | 51.096 | 106.09 | 92.26 | 106.09 | 51.10 | 51.10 |
| Relative width of pore size distribution [nm] | 73.7 | 79.7 | 102.1 | 70.9 | 28.45 | 36.0 |
| Moldability A: hardness (N) | 200.0 | 81.0 | 75.0 | 63.0 | 59.5 | 73.0 |
| Moldability B: hardness (N) | 48.0 | 38.0 | 30.5 | 32.3 | 26.0 | 29.3 |
| Moldability C: hardness (N) | 142.0 | 134.0 | 125.0 | 130.6 | 106.0 | 122.8 |

TABLE 2

|  | Example 7 | Example 8 |
|---|---|---|
| Oil absorption capacity [mL/g] | 3.64 | 3.96 |
| Static specific volume [mL/g] | 30.23 | 11.56 |
| Dynamic specific volume [mL/g] | 20.93 | 7.55 |
| Average particle diameter [μm] | 2.955 | 27.76 |
| BET specific surface area [m$^2$/g] | 345 | 336 |
| Pore volume [cm$^2$/g] | 1.61 | 2.14 |
| Pore mode diameter [nm] | 44.14 | 44.14 |
| Relative width of pore size distribution [nm] | 64.9 | 68.4 |

TABLE 3

|  | Comparative Example 1 | Comparative Example 2 | Comparative Example 3 | Comparative Example 4 | Comparative Example 5 | Comparative Example 6 |
|---|---|---|---|---|---|---|
| Oil absorption capacity [mL/g] | 2.52 | 2.22 | 2.26 | 1.02 | 2.00 | 2.02 |
| Static specific volume [mL/g] | 14.72 | 10.29 | 4.16 | 3.30 | 4.35 | 21.99 |
| Dynamic specific volume [mL/g] | 11.53 | 7.77 | 3.48 | 2.44 | 3.60 | 17.26 |
| Average particle diameter [μm] | 3.9 | 3.1 | 155.9 | 10.8 | 35 | 0.01 |
| BET specific surface area [m$^2$/g] | 324 | 345 | 306 | 484 | 276 | 193 |
| Pore volume [cm$^2$/g] | 2.09 | 1.63 | 1.72 | 0.71 | 1.78 | 0.80 |
| Pore mode diameter [nm] | 28.25 | 21.30 | 28.25 | 8.06 | 51.10 | 167.78 |
| Relative width of pore size distribution [nm] | 2.86 | 3.07 | 0.81 | 5.33 | 2.63 | 96.83 |
| Moldability A: hardness (N) | Poor | Poor | Poor | Poor | Poor | Poor |
| Moldability B: hardness (N) | 8.8 | Poor | Poor | Poor | 10.8 | Poor |
| Moldability C: hardness (N) | 27.0 | — | 21.3 | Poor | 55.3 | — |

TABLE 4

Comparison of friability

| | Tablet sample | | | |
|---|---|---|---|---|
| | Powder of Example 6 | Powder of Comparative Example 1 | Powder of Comparative Example 2 | Powder of Comparative Example 3 |
| Friability (%) | 0.144 | 0.259 | 0.242 | 0.231 |

In the evaluation of moldability, "poor" indicates that the sample was not compression molded at all, or the sample was disintegrated in an extremely short time from the removal from the die. Those indicated with numerical value represents the hardness measured due to no tableting problems.

Example 9

74% of 7:3 mixture of 200 M lactose and corn starch, 20% of microcrystalline cellulose (Ceolus PH-101, manufactured by Asahi Kasei Corporation), 5% of amorphous silica powder of Example 6, and 1% of magnesium stearate were mixed at the above ratio and tableted with a rotary tableting machine VIRGO manufactured by KIKUSUI SEISAKUSHO LTD. by using an φ8 flat punch at a rate of 200 mg/tablet and a rotational speed of 30 rpm as a setting hardness of 70N. The tablet friability test of the Japanese Pharmacopoeia was conducted on the obtained tablet. Tablets of the silica of Comparative Examples 1, 2, and 6 were also prepared by the same operation and the friability was measured.

When blended into a tablet, the porous silica powder of the present invention reduced the friability of the tablet more than the commercially available silica powders shown in Comparative Examples.

Example 10

The tablet prepared in Example 9 was stored in a thermostatic bath at 40° C. and 75% RH in an open state, and the disintegration test of the Japanese Pharmacopoeia was conducted 1, 2, and 4 weeks after. A load cell type tablet hardness tester PC-30 manufactured by OKADA SEIKO CO., LTD. was used for the hardness measurement. A disintegration tester NT-400 manufactured by TOYAMA SANGYO CO., LTD. was used for the disintegration test.

TABLE 5

Change of disintegration time

| Tablet sample | | Powder of Example 6 | Powder of Comparative Example 1 | Powder of Comparative Example 2 | Powder of Comparative Example 3 |
|---|---|---|---|---|---|
| Disintegration time (seconds) | Initial | 20 | 14 | 13 | 15 |
| | 1 week | 23 | 22 | 31 | 22 |
| | 2 weeks | 20 | 29 | 37 | 23 |
| | 4 weeks | 21 | 42 | 51 | 39 |

When blended into a tablet, the porous silica powder of the present invention causes no delay in the disintegration time as compared with the commercially available silica powders shown in Comparative Examples, even by storing under humidified conditions of 40° C. and 75% RH.

Example 11

[Formulation Example: Oil-Containing OD Agent]

A hemp seed oil (product name Biotuscany, manufactured by s.r.l) adsorbed with the porous silica particle composition of Example 6 in the ratio shown in the following table was powderized and mixed with F-MELt Type C (product name, an excipient for orally rapidly disintegrating tablets manufactured by Fuji Chemical Industries Co., Ltd.), microcrystalline cellulose (Ceolus PH-101, manufactured by Asahi Kasei Corporation), calcium hydrogen phosphate (Fujicalin SG, manufactured by Fuji Chemical Industries Co., Ltd.), corn starch (manufactured by Japan Corn Starch Co., Ltd), crospovidone (Kollidon CL-F, manufactured by BASF), 2:1 powder of the porous silica particle composition of Example 6 and a strawberry flavor, aspartame (manufactured by AJINOMOTO CO., INC.), magnesium stearate (manufactured by Nippon Oil and Fats Company, Limited), and the porous silica particle composition of Example 6, and then tableted with a rotary tableting machine (VIRGO, manufactured by KIKUSUI SEISAKUSHO LTD.) by using a φ10 flat punch under the conditions of a rate of 350 mg/tablet, a setting hardness of 55N, and a rotational speed of 40 rpm.

TABLE 6

| Formulation Example (tablet) | | Example 11 (%) | Comparative Example 7 (%) |
|---|---|---|---|
| Adsorbing powder | Hemp seed oil | 8.57 | 8.57 |
| | Porous silica particle composition of Example 6 | 8.57 | 8.57 |
| Post addition | F-MELT Type C | 36.86 | 39.86 |
| | Microcrystalline cellulose | 15.00 | 15.00 |
| | Anhydrous calcium hydrogen phosphate | 10.00 | 10.00 |
| | Corn starch | 10.00 | 10.00 |
| | Crospovidone | 5.00 | 5.00 |

TABLE 6-continued

| Formulation Example (tablet) | Example 11 (%) | Comparative Example 7 (%) |
|---|---|---|
| Porous silica particle composition of Example 6 | 3.00 | — |
| Strawberry flavor:Porous silica particle composition of Example 6(2:1)Adsorbing powder | 1.50 | 1.50 |
| Aspartame | 1.00 | 1.00 |
| Magnesium stearate | 0.50 | 0.50 |

TABLE 7

Tablet evaluation

| | Example 11 | Comparative Example 7 |
|---|---|---|
| Weight (mg) | 350.6 ± 0.733 | 349.6 ± 1.403 |
| Hardness (N) | 56.8 ± 2.201 | 53.7 ± 2.406 |
| Disintegration time (seconds) | 13.8 | 17.0 |
| Oral disintegration (seconds) | 24 | 30 |
| Tableting pressure (N) | 11.0 ± 0.16 | 15.2 ± 0.44 |

Figure 6:
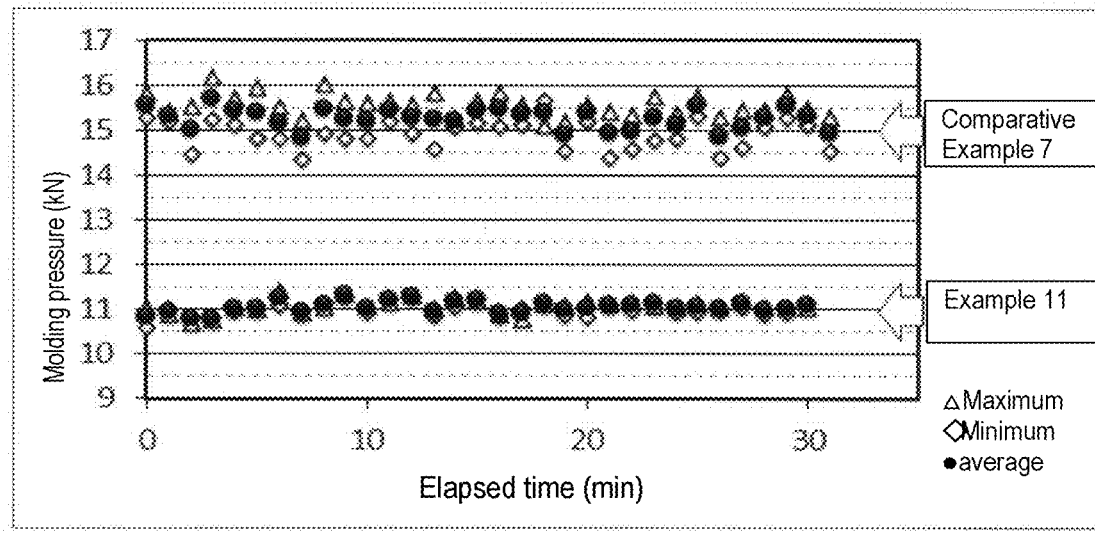
FIG. 6 is a graph showing the change over time of the molding pressure at the time of tableting of Example 11 and Comparative Example 7.
Figure 7:
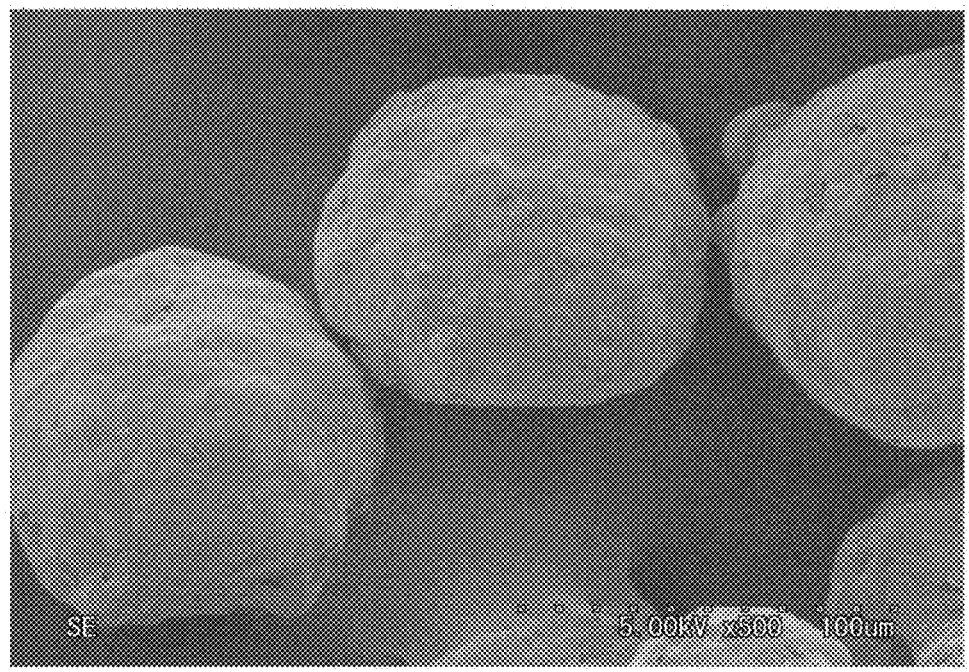
FIG. 7 is an SEM photograph (500 times) of the bitterness-masking particles of Example 16.

The OD tablet of Example 11 in which the silica particle composition of the present invention was post-added had a shorter disintegration time than the OD tablet of Comparative Example 7 with no post addition. Further, a tableting powder adsorbed with an oil generally has a poor moldability. Since the molding pressure varies as shown in Comparative Example 7 in FIG. 6, variations in the weight occur as seen from Table 7. The post addition of the silica particle composition of the present invention can result in the reduction of the molding pressure at the time of tableting and the decrease in the variations of the molding pressure like Example 11 in FIG. 6, and the decrease of the variations in the weight like Table 7.

Example 12

Formulation Example: Solid Dispersion

Itraconazole and the porous amorphous silica powder of Example 6 were mixed in a ratio of 7:3 with a mixed solvent of dichloromethane/ethanol (8/2=v/v), and drying was carried out by using a Mini Spray Dryer B-290 manufactured by Nihon BUCHI K.K. at a heat input of 70° C. and an exhaust heat of 50° C. to obtain a white powder of a solid dispersion of itraconazole. The same operation was carried out for Comparative Examples 3 and 4 to obtain white powders of a solid dispersion of itraconazole. Also, a spray dried product containing only itraconazole was prepared. To observe the stability of these samples, they were stored at 40° C. and 75% RH in an open state for one month. Each sample was collected such that the itraconazole content could be 30 mg and added to 500 mL of the first fluid of the Japanese Pharmacopoeia at 37° C. in accordance with the dissolution test of the Japanese Pharmacopoeia, and then the amount of itraconazole dissolved was measured at a specific elapsed time (30, 60, and 120 minutes). The measured value immediately after production was recorded in column A and the measured value of the sample stored at 40° C. and 75% RH in an open state for one month was recorded in column B.

TABLE 8

Dissolution test Amount of itraconazole dissolved (μg/mL)

| Elapsed time (minutes) | Spray dried powder of itraconazole | | Solid dispersion prepared from the powder of Example 6 | | Solid dispersion prepared from the powder of Comparative Example 3 | | Solid dispersion prepared from the powder of Comparative Example 4 | |
|---|---|---|---|---|---|---|---|---|
| | A | B | A | B | A | B | A | B |
| 30 | 27.5 | 22.9 | 53.8 | 50.4 | 42.8 | 22.0 | 45.7 | 26.9 |
| 60 | 35.0 | 28.9 | 54.2 | 52.2 | 45.5 | 26.4 | 46.8 | 33.2 |
| 120 | 43.6 | 35.3 | 56.3 | 54.7 | 49.7 | 34.0 | 48.6 | 42.1 |

The porous powder of the present invention can form the solid dispersion of itraconazole, and the porous powder and the solid dispersion of itraconazole has a higher dissolution of itraconazole than that in the silica of Comparative Example, that is, indicating a high stability.

Example 13

Formulation Example: Solid Dispersion

Nifedipine and copovidone (Kollidon VA64, manufactured by BASF) and the porous amorphous silica powder of Example 6 were mixed in a ratio of 9:1:3 with a mixed solvent of dichloromethane/ethanol (8/2=v/v), and drying was carried out by using a Mini Spray Dryer B-290 manufactured by Nihon BUCHI K.K. at a heat input of 70° C. and an exhaust heat of 50° C. to obtain a powder of a solid dispersion of nifedipine. The same operation was carried out for Comparative Examples 3 and 4 to obtain powders of a solid dispersion of nifedipine. Also, spray drying was carried out for the mixture of only nifedipine and copovidone to obtain a powder. To observe the stability of these samples, they were stored at 40° C. and 75% RH in an open state for one week. Each sample was collected such that the nifedipine content could be 7 mg and added to 500 mL of the second fluid of the Japanese Pharmacopoeia at 37° C. in accordance with the dissolution test of the Japanese Pharmacopoeia, and then the amount of nifedipine dissolved was measured at a specific elapsed time (30, 60, and 120 minutes). The value measured immediately after production was recorded in column A and the measured value of the sample stored at 40° C. and 75% RH in an open state for one week was recorded in column B.

TABLE 9

Dissolution test Amount of the solid dispersion of nifedipine dissolved (μg/mL)

| Elapsed time (minutes) | Spray dried powder of nifedipine and copovidone | | Solid dispersion prepared from the powder of Example 6 | | Solid dispersion prepared from the powder of Comparative Example 3 | | Solid dispersion prepared from the powder of Comparative Example 4 | |
|---|---|---|---|---|---|---|---|---|
| | A | B | A | B | A | B | A | B |
| 30 | 2.3 | 2.2 | 4.9 | 4.3 | 3.0 | 2.6 | 3.1 | 2.8 |
| 60 | 2.8 | 2.7 | 5.9 | 5.5 | 4.3 | 3.7 | 4.4 | 4.1 |
| 120 | 3.7 | 3.4 | 7.1 | 6.6 | 5.9 | 4.6 | 5.7 | 5.4 |

Example 14

Formulation Example: Solid Dispersion

For the porous amorphous silica powders of Examples 7 and 8, solid dispersions of itraconazole were produced in the same manner as in Example 12, and the dissolution test was conducted.

TABLE 10

Dissolution test Amount of itraconazole dissolved (μg/mL)

| Elapsed time (minutes) | Solid dispersion prepared from the powder of Example 7 | Solid dispersion prepared from the powder of Example 8 |
|---|---|---|
| 30 | 50.0 | 49.4 |
| 60 | 51.1 | 51.3 |
| 120 | 52.8 | 53.2 |

Example 15

Formulation Example: Bitterness Masking OD Tablet

Diphenhydramine hydrochloride was dissolved in a suitable amount of water and adsorbed to the porous amorphous silica powder of Example 6, and then dried. The powder was put into a fluidized bed granulation apparatus and an aqueous hydroxypropyl methyl cellulose solution was sprayed thereto to obtain a white powder. After the powder, F-MELT, The porous powder of the present invention can form the solid dispersion of nifedipine, and the solid dispersion prepared from the porous powder has a higher dissolution of nifedipine than that in the silica of Comparative Examples, that is, indicating a high stability.

starch, and magnesium stearate were mixed, the mixture was compression molded to obtain an orally rapidly disintegrating tablet of diphenhydramine hydrochloride. The compression molding was carried out with a rotary tableting machine HT-AP18SS-II of HATA TEKKOSHO CO., LTD. by using a φ9 flat punch at a rotational speed of 20 rpm and a setting hardness of 70 N. Respective ingredients were blended to be the following amount blended for the tablet.

| | |
|---|---|
| Diphenhydramine hydrochloride | 4 mg |
| Porous amorphous silica powder | 8 mg |
| Hydroxypropyl methyl cellulose | 6 mg |
| F-MELT | 50 mg |
| Starch | 80.5 mg |
| Magnesium stearate | 1.5 mg |
| (Total 150 mg/tablet) | |

<Sensory Test>

When a tablet was put into the mouth of five adults and the presence or absence of the bitterness was confirmed, all five adults replied "no bitterness".

<Dissolution Test>

The amount of diphenhydramine hydrochloride dissolved was measured for the obtained tablet based on the dissolution test of the Japanese Pharmacopoeia by using water as an eluent at 37° C. and by putting the tablet into 900 mL of the test solution.

TABLE 11

Dissolution rate of diphenhydramine formulation

| | Elapsed time (minutes) | |
|---|---|---|
| | 5 | 15 |
| Dissolution rate (%) | 95.2 | 93.6 |

An orally disintegrating tablet having a sufficient bitterness masking and causing no dissolution inhibition due to masking could be produced.

Example 16

100 g of porous silica powder of Example 6 was put into a fluidized bed granulator (Multiplex MP-01, manufactured by Powrex Corp.), and a solution obtained by dissolving 40 g of diphenhydramine hydrochloride in 160 g of water was sprayed thereto under the conditions of a supply air temperature from 55 to 60° C., an exhaust temperature from 26 to 29° C., an air volume from 0.3 to 0.5 m³/h, and a flow rate from 7 to 8 g/min. Then, after a solution obtained by dissolving and suspending 95.6 g of ethyl acrylate-methyl methacrylate copolymer dispersion (Eudragit NE30D, manufactured by Evonik), 18.8 g of methyl cellulose (METOLOSE SM-4, manufactured by Shin-Etsu Chemical Co., Ltd.), and 23.9 g of talc (manufactured by Nippon Talc Co., Ltd.) in 840 g of water was sprayed thereto under the same conditions, a solution obtained by dissolving 4.4 g of mannitol (mannite P, manufactured by Mitsubishi Shoji Foodtech Co., Ltd.) in 39.6 g of water was sprayed thereto under the same conditions to obtain drug bitterness-masking particles (average particle diameter: 136.8 μm).

Example 17

After 20 g of the porous silica powder of Example 6 was stirred with a stirrer (HEIDON1200G, manufactured by Shinto Scientific Co., Ltd.), a solution obtained by dissolving 10 g of diphenhydramine hydrochloride in 6 g of water was gradually added thereto, and the mixture was stirred for 1 minute, and then dried in a shelf dryer at 70° C. overnight to obtain a powder. Then, after the total amount of the powder and 3 g of microcrystalline cellulose (Ceolus PH-101, manufactured by Asahi Kasei Corporation) were put into a stirring granulator, 66 g of ethyl acrylate-methyl methacrylate copolymer dispersion was gradually added thereto, and the mixture was stirred for 2 minutes to obtain a wet powder. This wet powder was dried at 70° C. overnight and sieved with a 15 mesh sieve to obtain spherical drug bitterness-masking particles.

Example 18

100 g of the porous silica powder of Example 6 was put into a fluidized bed granulator, and a solution obtained by dissolving 20 g of diphenhydramine hydrochloride and 20 g of ethyl cellulose (ETHOCEL, manufactured by Colorcon) in 760 g of ethanol was sprayed thereto under the conditions of a supply air temperature of 60° C., an exhaust temperature from 28 to 30° C., an air volume from 0.3 to 0.4 m³/h, and a flow rate from 12 to 13 g/mL to obtain drug bitterness-masking particles.

Example 19

20 g of the porous silica powder of Example 6 was stirred with a stirrer (HEIDON1200G, manufactured by Shinto Scientific Co., Ltd.), a solution obtained by dissolving 10 g of diphenhydramine hydrochloride in 6 g of water was added thereto, and the mixture was stirred for 1 minute. Then, after 3 g of microcrystalline cellulose (Ceolus PH-101, manufactured by Asahi Kasei Corporation) was added thereto, 66 g of ethyl acrylate-methyl methacrylate copolymer dispersion was added thereto, and the mixture was stirred for 1 minute to obtain a powder. This powder was dried at 70° C. overnight and sieved with a 15 mesh sieve to obtain spherical drug bitterness-masking particles.

Example 20

200 g of the porous silica powder of Example 6 was put into a high-speed stirring granulator (NMG-5L, manufactured by NARA MACHINERY CO., LTD.), a solution obtained by dissolving 100 g of diphenhydramine hydrochloride in 60 g of water was gradually added thereto, the mixture was stirred for 1 minute, and then, dried with a shelf dryer at 70° C. overnight to obtain a powder. Then, the total amount of the powder and 45 g of crystalline cellulose were put into a stirring granulator, 990 g of ethyl acrylate-methyl methacrylate copolymer dispersion was gradually added thereto, and the mixture was stirred for 1 minute to obtain a wet powder. This wet powder was dried at 70° C. overnight and sized by using a comil to obtain spherical drug bitterness-masking particles.

Comparative Example 8

Drug-containing particles were obtained in the same manner as in Example 16 except that the porous silica powder of Example 6 was replaced with silicon dioxide (Adsolider 101, manufactured by Freund Corporation).

Comparative Example 9

Drug-containing particles were obtained in the same manner as in Example 16 except that the porous silica powder of Example 6 was replaced with silicon dioxide (Aeroper1300, sphericity: 0.93, manufactured by Evonik). However, since a load was exerted on the apparatus, the amount of ethyl acrylate-methyl methacrylate copolymer dispersion added was changed to 33 g.

Comparative Example 10

Drug-containing particles were obtained in the same manner as in Example 16 except that the porous silica powder of Example 6 was replaced with silicon dioxide (Syloid XDP3150, sphericity: 0.68, manufactured by Grace). However, since a load was exerted on the apparatus, the amount of ethyl acrylate-methyl methacrylate copolymer dispersion added was changed to 33 g.

[Syringe Barrel Inversion Test]

The sample powder corresponding to 10 mg of diphenhydramine hydrochloride was added to 10 mL of water, gently mixed at a rotational speed of one rotation per about two to three seconds for 10 seconds, filtered with a filter, and then the filtrate was measured with an absorption spectrometer at a measurement wavelength of 258 nm to determine the concentration of diphenhydramine hydrochloride.

When the amount of diphenhydramine hydrochloride dissolved is about 0.4 mg/mL or less, almost no bitter taste is felt and from about 0.4 to 0.6 mg/mL is a standard at which the bitter taste can be masked by adding a taste masking agent, a sweetening agent, a fragrance, and the like.

TABLE 12

Amount of drug dissolved

| | Comparative Example 8 | Comparative Example 9 | Comparative Example 10 | Example 16 | Example 17 | Example 18 | Example 19 | Example 20 |
|---|---|---|---|---|---|---|---|---|
| Amount of drug dissolved [mg/mL] | 0.74 | 0.77 | Degradation product | 0.08 | 0.34 | 0.36 | 0.34 | 0.45 |

The amount of the drug of Comparative Examples 8 to 10 dissolved was 0.7 mg/mL or more and the bitterness masking is not achieved, whereas the amount of the drug of Examples 15 to 19 dissolved was 0.4 mg/mL or less and the bitterness was masked. Since the light absorbing pattern was changed in Comparative Example 9, the occurrence of a degradation product was confirmed.

[Orally Rapidly Disintegrating Tablet]

The bitterness-masking particles of Examples 16 to 20, each corresponding to 20 g of the drug, 446.4 g of F-MELT Type C (manufactured by Fuji Chemical Industries Co., Ltd.), 30.0 g of crospovidone (Kollidon CL-F, manufactured by BASF), 6.0 g of acesulfame potassium (Sunett, manufactured by MC Food Specialties Inc.), 6.0 g of aspartame (manufactured by AJINOMOTO), and 6.0 g of magnesium stearate (manufactured by NOF CORPORATION) were mixed, and a tablet was obtained by using a ϕ9 flat punch at a setting of a rotational speed of 20 rpm, a compression pressure from 600 to 700, a tablet weight of 300 mg, and a setting hardness from 70 to 80N.

[Bitterness Sensory Test]

The particles of Comparative Examples 8 to 9 and Examples 16 to 20, and the tablets of Examples 21 to 25 were put in the mouth for 30 seconds, and the bitter taste of the drug was evaluated by five people. The bitter taste was evaluated based on the following criteria, and the average thereof was determined.
3: Bitterness is strongly felt
2: Bitterness is felt
1: No bitter taste is felt

TABLE 13

Bitterness sensory test of bitterness-masking particles

| | Comparative Example 8 | Comparative Example 9 | Example 16 | Example 17 | Example 18 | Example 19 | Example 20 |
|---|---|---|---|---|---|---|---|
| Evaluation | 3 | 3 | 1 | 1.4 | 1.2 | 1.4 | 1.6 |

TABLE 14

Bitterness sensory test of orally rapidly disintegrating tablet

| | Example 16 | Example 17 | Example 18 | Example 19 | Example 20 |
|---|---|---|---|---|---|
| Evaluation | 1 | 1 | 1 | 1 | 1.2 |

The particles of Comparative Examples 8 to 9 were 3 or more and thus the bitterness was strongly felt, whereas the bitterness-masking particles of Examples 15 to 19 were 1.6 or less and the bitterness was only slightly felt, and thus the bitterness was masked. The bitterness-masking particles of Examples 16 to 19 were 1.2 or less, and almost no bitterness was felt in the orally rapidly disintegrating tablets in which the sweetening agent and the like are blended.

[Dissolution Test]

For the tablet of Example 16, the dissolution rate of diphenhydramine was measured in accordance with the dissolution test method of the Japanese Pharmacopoeia.

TABLE 15

| Dissolution rate (%) | |
|---|---|
| Dissolution time | Example 16 |
| 5 minutes | 90.3 |
| 10 minutes | 98.4 |
| 15 minutes | 100.9 |

The tablet of Example 16 in which the drug was subjected to bitterness masking, showed a dissolution behavior equivalent to that of Comparative Example 1 to which no masking was subjected, and was excellent in dissolution properties.

The invention claimed is:

1. A porous silica particle composition having following properties:
   (1) a BET specific surface area from 250 to 1,000 $m^2/g$;
   (2) an average particle diameter from 1 to 150 µm;
   (3) a pore volume from 0.1 to 8.0 $cm^3/g$; and
   (4) an oil absorption capacity from 2.2 to 5.0 mL/g,
   wherein a relative width of a pore size distribution is from 20 to 120 nm.

2. The porous silica particle composition according to claim 1, wherein
   (1) the BET specific surface area is from 250 to 700 $m^2/g$;
   (2) the average particle diameter is from 1 to 40 µm;
   (3) a static specific volume is from 8 to 40 mL/g;
   (4) the oil absorption capacity is from 2.2 to 5.0 mL/g; and
   (5) a water absorption capacity is from 2.2 to 5.0 mL/g.

3. The porous silica particle composition according to claim 1, wherein the average particle diameter is from 1 to 30 µm and a shape is substantially non-spherical.

4. The porous silica particle composition according to claim 1, wherein a static specific volume is from 20 to 40 mL/g.

5. The porous silica particle composition according to claim 1, wherein the porous silica particle composition is amorphous.

6. The porous silica particle composition according to claim 1, wherein the pore volume is from 1.0 to 2.5 $cm^3/g$.

7. The porous silica particle composition according to claim 1, wherein a pore mode diameter is from 20 to 150 nm.

8. The porous silica particle composition according to claim 1, comprising primary particles comprising plate-like silica particles having a particle diameter of from 20 to 500 nm and spherical silica particles having a particle diameter of from 5 to 50 nm,
   wherein the primary particles are agglomerated to form the porous silica particle composition.

9. The porous silica particle composition according to claim 1, wherein the oil absorption capacity is from 2.4 to 4.5 mL/g.

10. The porous silica particle composition according to claim 1, wherein a static specific volume is from 4.5 to 8 mL/g.

11. The porous silica particle composition according to claim 1, wherein the BET specific surface area is from 280 to 650 $m^2/g$.

12. The porous silica particle composition according to claim 1, wherein the average particle diameter is from 30 to 120 µm.

13. The porous silica particle composition according to claim 1, wherein sphericity of a-particle in the porous silica particle compositions is from 0.8 to 1.0.

14. The porous silica particle composition according to claim 1, wherein the porous silica particle composition is a pharmaceutical excipient, a supplement, a health food, or a cosmetic excipient.

15. An additive, comprising:
    the porous silica particle composition according to claim 1,
    wherein the additive is suitable for pharmaceutical, supplemental, health food, or cosmetic.

16. A pharmaceutical formulation, supplement, health food, or cosmetic product, comprising:
    the porous silica particle composition according to claim 1.

17. A pharmaceutical composition, comprising:
    the porous silica particle composition according to claim 1,
    a polymer, and
    a bitter drug.

18. A solid dispersion obtained by dispersing an active pharmaceutical ingredient in the porous silica particle composition according to claim 1.

* * * * *